United States Patent
Ramsey et al.

(10) Patent No.: US 10,864,520 B2
(45) Date of Patent: Dec. 15, 2020

(54) FLUIDIC DEVICES WITH FREEZE-THAW VALVES WITH ICE-NUCLEATING AGENTS AND RELATED METHODS OF OPERATION AND ANALYSIS

(71) Applicant: The University of North Carolina at Chapel Hill, Chapel Hill, NC (US)

(72) Inventors: John Michael Ramsey, Chapel Hill, NC (US); William Hampton Henley, Chapel Hill, NC (US); Joseph Carl Gaiteri, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 348 days.

(21) Appl. No.: 15/742,662

(22) PCT Filed: Jul. 22, 2016

(86) PCT No.: PCT/US2016/043463
§ 371 (c)(1),
(2) Date: Jan. 8, 2018

(87) PCT Pub. No.: WO2017/015529
PCT Pub. Date: Jan. 26, 2017

(65) Prior Publication Data
US 2018/0200720 A1 Jul. 19, 2018

Related U.S. Application Data

(60) Provisional application No. 62/195,652, filed on Jul. 22, 2015.

(51) Int. Cl.
*F16K 99/00* (2006.01)
*B01L 7/00* (2006.01)
(Continued)

(52) U.S. Cl.
CPC ............ *B01L 7/50* (2013.01); *B01L 3/502738* (2013.01); *C07K 14/195* (2013.01); *C07K 14/21* (2013.01);
(Continued)

(58) Field of Classification Search
None
See application file for complete search history.

(56) References Cited

U.S. PATENT DOCUMENTS

| 4,200,228 A | 4/1980 | Woerpel |
| 4,203,472 A | 5/1980 | Dulaney |

(Continued)

FOREIGN PATENT DOCUMENTS

| CN | 101995477 | 3/2011 |
| EP | 0 307 712 A2 | 3/1989 |

(Continued)

OTHER PUBLICATIONS

Batz et al. "Chemical Vapor Deposition of Aminopropyl Silanes in Microfluidic Channels for Highly Efficient Microchip Capillary Electrophoresis-Electrospray Ionization-Mass Spectrometry" *Analytical Chemistry* 86:3493-3500 (2014).
(Continued)

*Primary Examiner* — Paul S Hyun
(74) *Attorney, Agent, or Firm* — Myers Bigel, P.A.

(57) ABSTRACT

Embodiments of the invention provide fluidic devices such as, but not limited to, microfluidic chips, with one or more freeze thaw valves (FTVs) employing one or more ice-nucleating agents (INAs), that can reliably operate to freeze at relatively higher temperatures and/or at faster rates than conventional microfluidic devices with FTV systems.

31 Claims, 15 Drawing Sheets

(51) Int. Cl.

| | | |
|---|---|---|
| C07K 14/21 | (2006.01) | |
| C07K 14/195 | (2006.01) | |
| C07K 14/27 | (2006.01) | |
| B01L 3/00 | (2006.01) | |
| C12N 15/115 | (2010.01) | |
| G01N 1/42 | (2006.01) | |

(52) U.S. Cl.
CPC ............ *C07K 14/27* (2013.01); *C12N 15/115* (2013.01); *F16K 99/0032* (2013.01); *F16K 99/0036* (2013.01); *F16K 99/0044* (2013.01); *G01N 1/42* (2013.01); *B01L 2300/0816* (2013.01); *B01L 2300/1894* (2013.01); *B01L 2400/0677* (2013.01); *C12N 2310/16* (2013.01); *F16K 2099/0084* (2013.01)

(56) References Cited

U.S. PATENT DOCUMENTS

| | | |
|---|---|---|
| 4,706,463 A | 11/1987 | Lindsey |
| 4,978,540 A | 12/1990 | Lee |
| 5,014,738 A | 5/1991 | Jones |
| 5,101,848 A | 4/1992 | Kojima et al. |
| 5,233,412 A | 8/1993 | Nishihara |
| 5,489,521 A | 2/1996 | So et al. |
| 5,532,160 A | 7/1996 | Watanabe et al. |
| 5,554,368 A | 9/1996 | Stack et al. |
| 5,620,729 A | 4/1997 | Watanabe et al. |
| 5,843,506 A | 12/1998 | Watanabe et al. |
| 5,972,686 A | 10/1999 | Kang et al. |
| 5,988,197 A | 11/1999 | Colin et al. |
| 6,007,302 A | 12/1999 | Welle |
| 6,311,713 B1 | 11/2001 | Kaartinen |
| 6,361,934 B1 | 3/2002 | Acton et al. |
| 6,557,575 B1 | 5/2003 | Gerhardt et al. |
| 6,575,188 B2 | 6/2003 | Parunak |
| 6,581,299 B1 | 6/2003 | Dedieu et al. |
| 7,128,081 B2 | 10/2006 | Dourdeville |
| 7,195,036 B2 | 3/2007 | Burns et al. |
| 7,204,265 B2 | 4/2007 | Zikeli et al. |
| 7,497,937 B2 | 3/2009 | Yeung et al. |
| 7,624,698 B2 | 12/2009 | Taylor et al. |
| 7,686,040 B2 | 3/2010 | Welle |
| 7,694,694 B2 | 4/2010 | Welle |
| 7,757,716 B2 | 7/2010 | Welle |
| 7,814,928 B2 | 10/2010 | Maltezos et al. |
| 7,841,109 B2 | 11/2010 | Stevens et al. |
| 8,037,903 B2 | 10/2011 | Wang et al. |
| 8,141,573 B2 | 3/2012 | Tai et al. |
| 8,235,073 B2 | 8/2012 | Namkoong et al. |
| 8,256,465 B2 | 9/2012 | Christenson et al. |
| 8,765,076 B2 | 7/2014 | Handique et al. |
| 8,851,103 B2 | 10/2014 | Kwon |
| 8,940,249 B2 | 1/2015 | Jaeggi et al. |
| 2008/0112855 A1 | 5/2008 | Lee et al. |
| 2008/0236668 A1 | 10/2008 | Beerling et al. |
| 2008/0280285 A1 | 11/2008 | Chen et al. |
| 2009/0146380 A1 | 6/2009 | Votaw et al. |
| 2010/0252124 A1 | 10/2010 | Kurt et al. |
| 2010/0276005 A1 | 11/2010 | Allain et al. |
| 2011/0056240 A1 | 3/2011 | Malik et al. |
| 2014/0102116 A1 | 4/2014 | Welle |
| 2014/0224349 A1 | 8/2014 | Ducrée et al. |

FOREIGN PATENT DOCUMENTS

| | | |
|---|---|---|
| JP | 2009192348 | 8/2009 |
| WO | WO 2007/092713 A2 | 8/2007 |

OTHER PUBLICATIONS

Beebe et al. "Functional hydrogel structures for autonomous flow control inside microfluidic channels" *Nature* 404:588-590 (2000).

Beis et al. "Two-step purification of outer membrane proteins" *International Journal of Biological Macromolecules* 39:10-14 (2006).

Cochet et al. "Ice crystallization by *Pseudomonas syringae*" *Applied Microbiology and Biotechnology* 54:153-161 (2000).

Deininger et al. "Immunological Characterization of Ice Nucleation Proteins from *Pseudomonas syringae, Pseudomonas fluorescens*, and *Erwinia herbicola*" *Journal of Bacteriology* 170(2):669-675 (1988).

Dittrich et al. "Micro Total Analysis Systems. Latest Advancements and Trends" *Analytical Chemistry* 78(12):3887-3907 (2006).

Eddington et al. "Flow control with hydrogels" *Advanced Drug Delivery Reviews* 56:199-210 (2004).

Fall et al. "Biochemistry of Bacterial Ice Nuclei" *Biological Ice Nucleation and its Applications* Chapter 4:63-83 (1995).

Govindarajan et al. "Phospholipid Requirement for Expression of Ice Nuclei in *Pseudomonas syringae* and in Vitro" *The Journal of Biological Chemistry* 263(19):9333-9338 (1988).

Green et al. "Physical and functional repetition in a bacterial ice nucleation gene" *Nature* 317:645-648 (1985).

Gui et al. "Microfluidic phase change valve with a two-level cooling/heating system" *Microfluidics and Nanofluidics* 10:435-445 (2011).

Gurian-Sherman et al. "Bacterial ice nucleation: significance and molecular basis" *The FASEB Journal* 7:1338-1343 (1993).

Hartshorne et al. "Ferrofluid-based microchip pump and valve" *Sensors and Actuators B* 99:592-600 (2004).

Henley et al. "Fabrication of Microfluidic Devices Containing Patterned Microwell Arrays" *Analytical Chemistry* 84:1776-1780 (2012).

Hobb et al. "Evaluation of procedures for outer membrane isolation from *Campylobacter jejuni*" *Microbiology* 155:979-988 (2009).

International Search Report and the Written Opinion of the International Searching Authority corresponding to International Patent Application No. PCT/US2016/043463 (11 pages) (dated Oct. 18, 2016).

Jacobson et al. "Microchip Structures for Submillisecond Electrophoresis" *Analytical Chemistry* 70:3476-3480 (1998).

Jacobson et al. "Minimizing the Number of Voltage Sources and Fluid Reservoirs for Electrokinetic Valving in Microfluidic Devices" *Analytical Chemistry* 71:3273-3276 (1999).

Kawahara, Hidehisa "The Structures and Functions of Ice Crystal-Controlling Proteins from Bacteria" *Journal of Bioscience and Bioengineering* 94(6):492-496 (2002).

Kim et al. "Purification and Characterization of Ice Nucleating Protein from *Pseudomonas syringae*" *Korean Journal of Biochemistry* 22(1):73-77 (1989).

Klintberg et al. "Fabrication of a paraffin actuator using hot embossing of polycarbonate" *Sensors and Actuators A* 103:307-316 (2003).

Liu et al. "Single-use, thermally actuated paraffin valves for microfluidic applications" *Sensors and Actuators B* 98:328-336 (2004).

Lorv et al. "Bacterial Ice Crystal Controlling Proteins" *Scientifica (Cairo)* 2014:1-20 (2014).

Manz et al. "Miniaturized Total Chemical Analysis Systems: a Novel Concept for Chemical Sensing" *Sensors and Actuators B* 1:244-248 (1990).

Martinez et al. "Diagnostics for the Developing World: Microfluidic Paper-Based Analytical Devices" *Analytical Chemistry* 82:3-10 (2010).

Neumann et al. "Design and characterization of a platform for thermal actuation of up to 588 microfluidic valves" *Microfluidics and Nanofluidics* 14:177-186 (2013).

Nie et al. "An automated integrated platform for rapid and sensitive multiplexed protein profiling using human saliva samples" *Lab on a Chip* 14:1087-1098 (2014).

Obata et al. "Properties of Cell-Free Ice Nuclei from Ice Nucleation-Active *Pseudomonas fluorescens* KUIN-1" *Journal of Fermentation and Bioengineering* 76(1):19-24 (1993).

Obata et al. "Identification of a Novel Ice-Nucleating Bacterium of Antarctic Origin and its Ice Nucleation Properties" *Cryobiology* 38:131-139 (1999).

(56) References Cited

OTHER PUBLICATIONS

Pitter et al. "A Wind Tunnel Investigation of the Rate of Evaporation of Large Water Drops Falling at Terminal Velocity in Air" *Quarterly Journal of the Royal Meteorological Society* 99(421):540-550 (1973) (Abstract Only).

Pouleur et al. "Ice Nucleation Activity in *Fusarium acuminatum* and *Fusarium avenaceum*" *Applied and Environmental Microbiology* 58(9):2960-2964 (1992).

Pruppacher et al. "A Wind Tunnel Investigation of the Rate of Evaporation of Large Water Drops Falling at Terminal Velocity in Air" *Journal of the Atmospheric Sciences* 36:1255-1260 (1979).

Reyes et al. "Micro Total Analysis System. 1. Introduction, Theory, and Technology" *Analytical Chemistry* 74:2623-2636 (2002).

Stan et al. "A microfluidic apparatus for the study of ice nucleation in supercooled water drops" *Lab on a Chip* 9:2293-2305 (2009).

Vali, Gabor "Principles of Ice Nucleation" *Biological Ice Nucleation and its Applications* Chapter 1:1-28 (1995).

Watabe et al. "Large-scale Production and Purification of an *Erwinia ananas* Ice Nucleation Protein and Evaluation of Its Ice Nucleation Activity" *Bioscience, Biotechnology, and Biochemistry* 57(4):603-606 (1993).

Whitesides, George M. "The origins and the future of microfluidics" *Nature* 442:368-373 (2006).

Wolber et al. "Identification and purification of a bacterial ice-nucleation protein" *Proceedings of the National Academy of Sciences USA* 83:7256-7260 (1986).

Zhou et al. "Recent developments in PDMS surface modification for microfluidic devices" *Electrophoresis* 31:2-16 (2010).

Chen et al. "Thermally-actuated, phase change flow control for microfluidic systems" Lab Chip, 5:1277-1285 (2005).

Si et al. "High response speed microfluidic ice valves with enhanced thermal conductivity and a movable refrigeration source" Scientific Reports, 7(40570):1-7 (2017).

Schmid et al. "Molecular organization of the ice nucleation protein InaV from Pseudomonas syringae" FEBS Letters, 414:590-594 (1997).

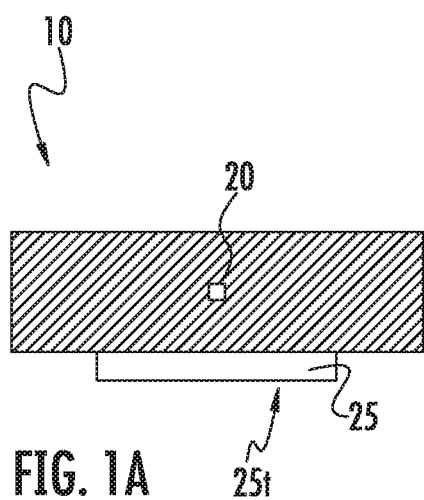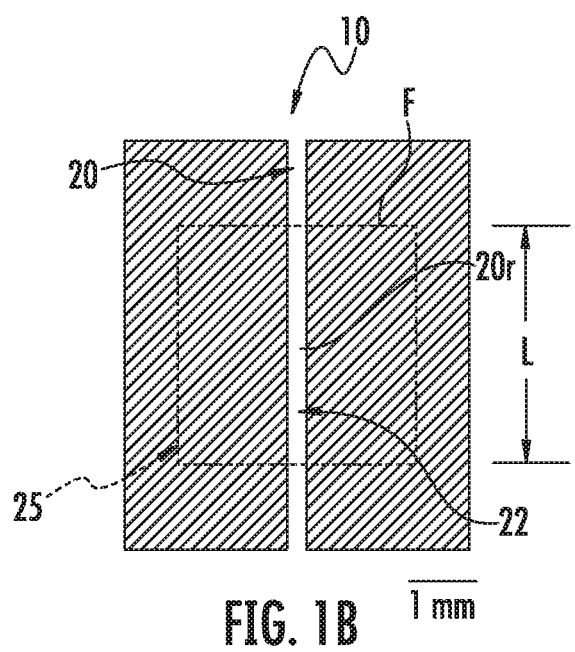

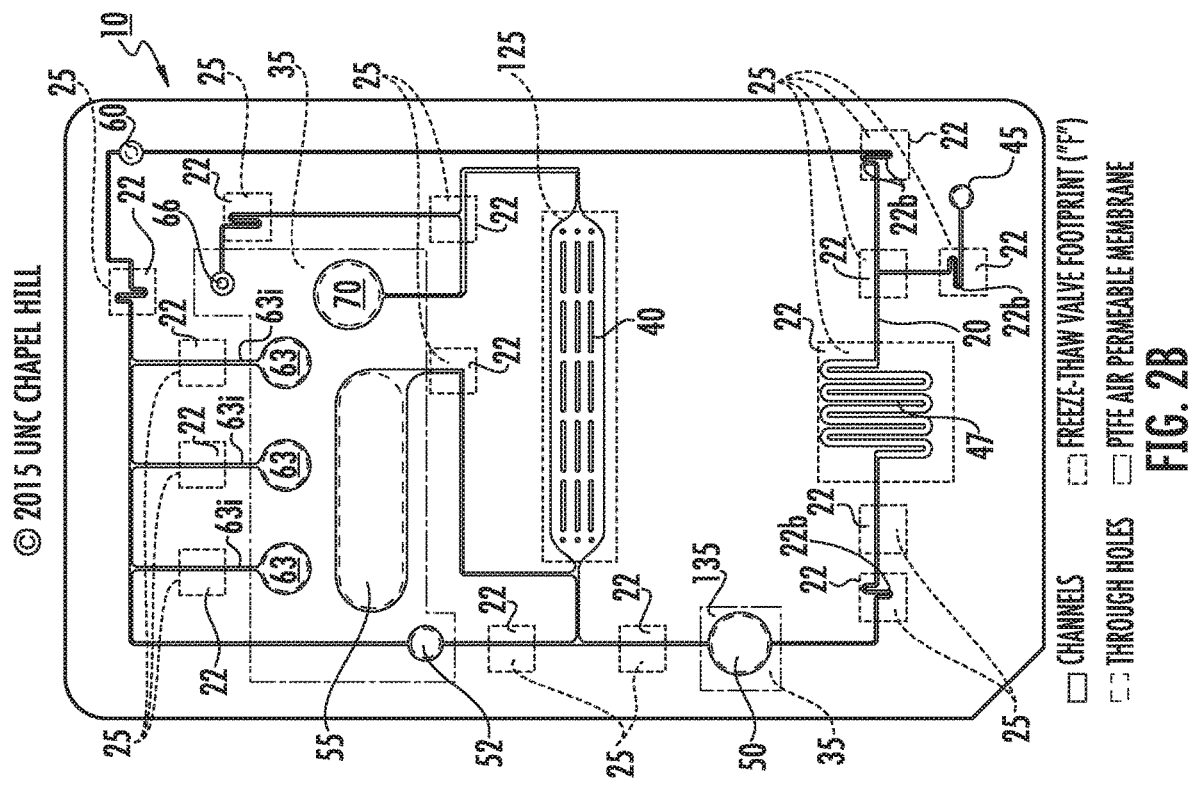
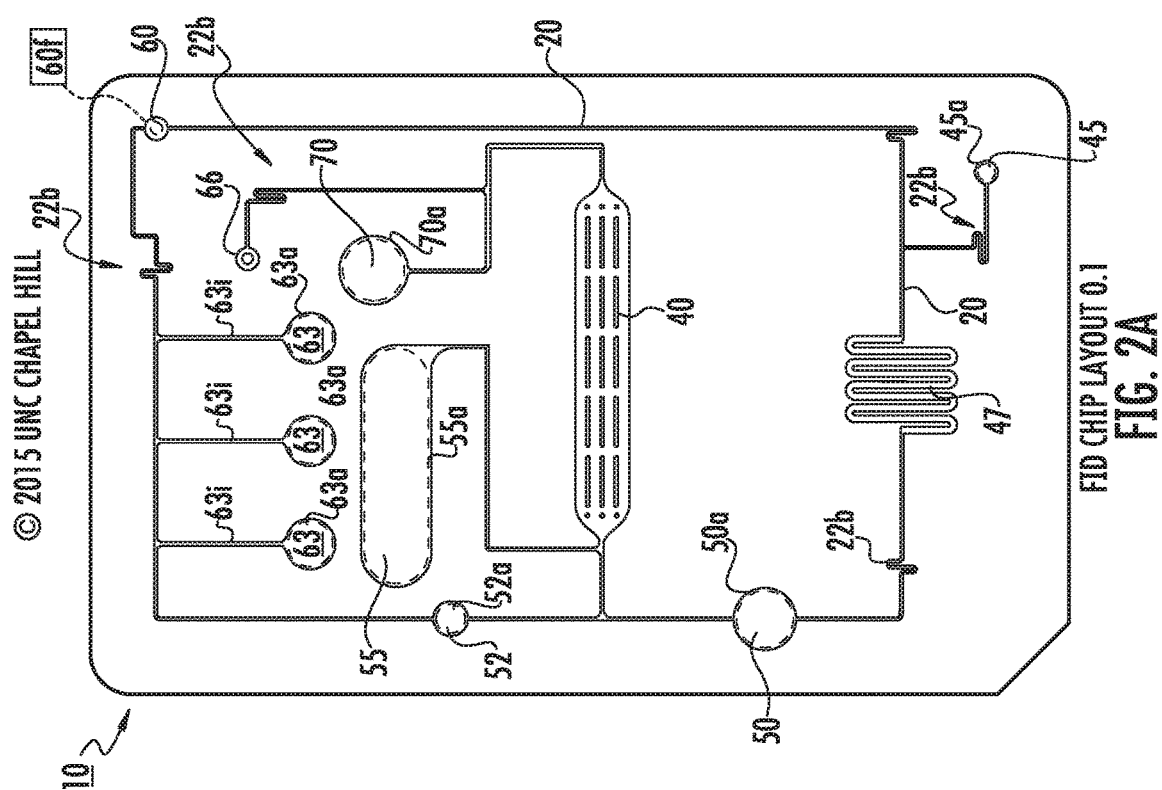

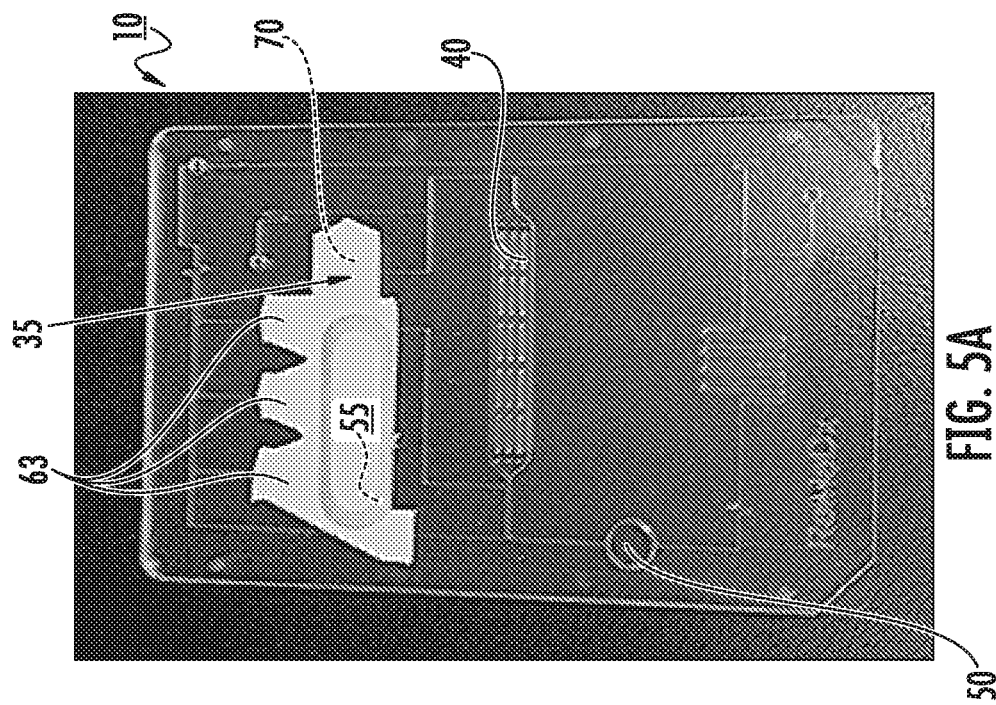
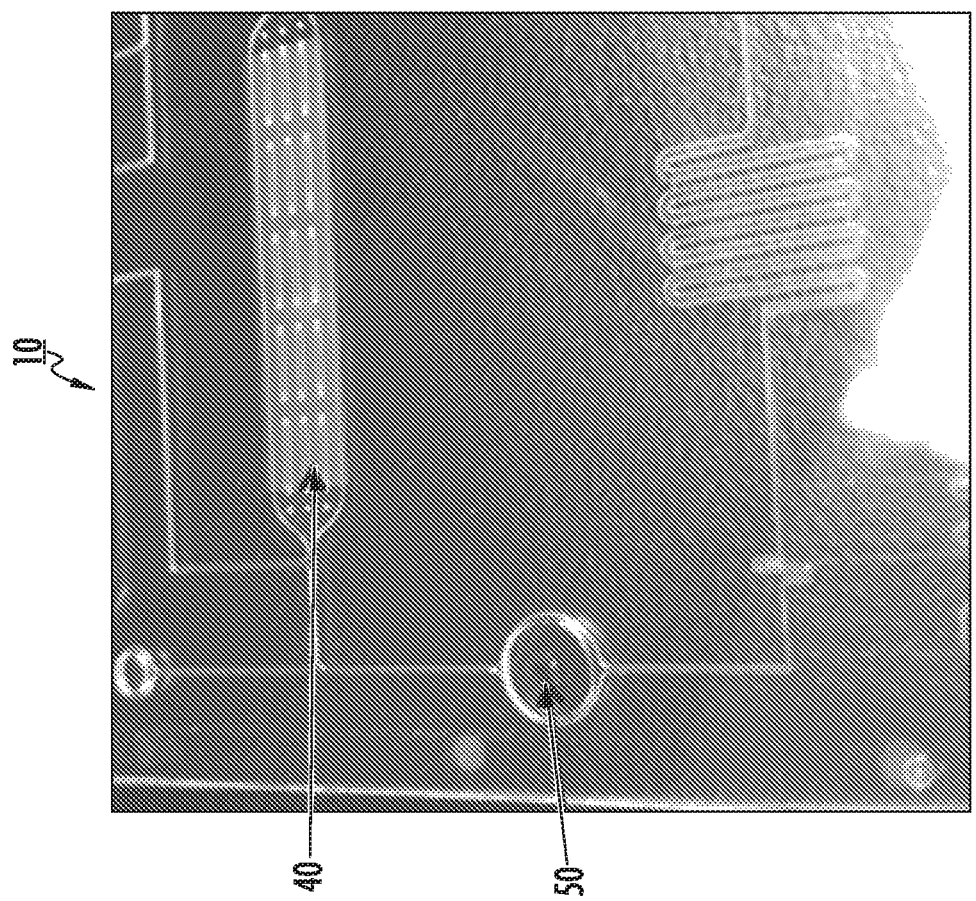
FIG. 5A
FIG. 5B

FLUIDIC DEVICES WITH FREEZE-THAW VALVES WITH ICE-NUCLEATING AGENTS AND RELATED METHODS OF OPERATION AND ANALYSIS

RELATED APPLICATIONS

This application is a 35 U.S.C. § 371 national stage application of PCT/US2016/043463, filed Jul. 22, 2016, which claims the benefit of and priority to U.S. Provisional Application Ser. No. 62/195,652, filed Jul. 22, 2015, the contents of which are hereby incorporated by reference as if recited in full herein.

STATEMENT OF FEDERAL SUPPORT

This invention was made with government support under Grant No. HR0011-12-2-0001 awarded by DOD Defense Advanced Research Projects Agency (DARPA). The government has certain rights in the invention.

RESERVATION OF COPYRIGHT

A portion of the disclosure of this patent document contains material which is subject to copyright protection. The copyright owner, The University of North Carolina at Chapel Hill, N.C., has no objection to the reproduction by anyone of the patent document or the patent disclosure, as it appears in the United States Patent and Trademark Office patent file or records, but otherwise reserves all copyright rights whatsoever.

FIELD OF THE INVENTION

This invention relates to fluidic devices for processing analytes for analysis.

BACKGROUND OF THE INVENTION

Microfluidic devices or chips have received a great deal of attention for their ability to manipulate and study minute quantities of liquid. See, e.g., Whitesides, G. M., The Origins and the Future of Microfluidics. *Nature* 2006, 442, 368-373. A variety of applications have been demonstrated with these devices, including chromatographic and electrophoretic separations, cell culture, and point-of-care medical diagnostics. In microfluidic systems that utilize multiple liquids or reagents, valves are often useful or necessary to modulate fluid flow. Freeze-thaw valves (FTVs) utilize an external cooling source such as a thermoelectric cooler (TEC) to freeze a plug of fluid in a channel, thus stopping fluid flow in the desired regions of the fluidic chip. The channel can then be opened by warming the plug until it thaws. However, implementation of FTVs has been hindered by the low temperatures needed to nucleate ice crystals on a microfluidic scale.

Liquid water does not necessarily nor immediately freeze below its melting point. When the temperature of liquid water drops below 0° C., it enters a metastable thermodynamic state (supercooling) in which small aggregates of a solid-like phase ("embryos") exist through the liquid phase. These embryos are decaying and growing in equilibrium with the liquid phase, and their average size can be proportional to the degree of supercooling. In order for the metastable liquid phase to transition to the stable solid phase (ice/frozen phase), embryo growth should be energetically more favorable and likely than decay. This occurs during a process known as "nucleation," of which there are two types. In pure liquids, nucleation occurs homogenously when the embryos reach a critical size and trigger continued growth of the solid phase. The probability of homogenous nucleation increases as the temperature of the supercooled phase drops. At approximately −35° C., the probability begins to increase by a factor of 50 with each successive 1° C. drop, and at approximately −40° C., the likelihood of homogenous nucleation approaches or reaches 100%. Above this temperature range, water can be nucleated heterogeneously with a foreign substance such as a mineral, dust, or pollen. Deep supercooling is not often observed on the macro scale because these nucleating impurities can be abundant.

Microfluidic devices typically have smooth channel walls and very small volumes, making nucleation sites rare. A high degree of supercooling, often to temperatures below −20° C., is typically needed to freeze water in most microfluidic devices. This increases the system's requirements for heat pumping and, in turn, power. Strong thermal contact between the microfluidic device and the cooling elements can also be a nontrivial design effort. Thin materials such as D263 glass are often used to increase or maximize heat pumping out of the channels. These thin glass materials can be fragile. Additionally, in the absence of nucleation sites, the reproducibility of successful valving events can have a high percent relative standard deviation (% RSD). These problems may be circumvented with the use of agents capable of nucleating ice at warm temperatures, but most have limited applications in microfluidic devices due to their water insolubility and/or constituents that can inhibit many biological processes and cause precipitation of many salts used in biological buffers. Also, many nucleators function best when dry and can lose much of their effectiveness when suspended in water. These considerations have limited the implementation of FTVs in microfluidic devices.

SUMMARY OF EMBODIMENTS OF THE INVENTION

Embodiments of the invention provide microfluidic chips with one or more FTVs employing one or more ice-nucleating agents (INAs) (e.g., one or more ice-nucleating proteins "INP" and/or functional fragment thereof and/or a microorganism comprising the same), that can reliably operate to freeze at relatively high temperatures and/or at faster rates than conventional microfluidic devices with FTV systems.

Embodiments of the invention provide INAs that can reliably function in aqueous solution and do not need to be dry, thereby allowing multiple valve actuations on a respective microfluidic device.

Embodiments of the invention can employ a substrate, such as, for example, polymer, glass, silicon, metal, or other substrates suitable for a microfluidic chip with FTVs.

Embodiments of the invention are directed to fluidic analysis devices that include at least one fluid channel with at least one freeze thaw valve and at least one ice nucleating agent (INA).

The at least one INA can include one or more of an ice-nucleating protein, an ice-nucleating nucleic acid, ice-nucleating lipid, and/or an ice-nucleating carbohydrate.

The at least one INA can be extracted and/or derived from an organism.

The at least one INA can include an ice-nucleating protein (INP) and/or a functional fragment thereof. Optionally, the INP and/or functional fragment thereof can be extracted from a membrane of *Pseudomonas syringae*.

The INP can be encoded by one or more of the following genes: iceE, iceH, inaA, inaE, inaF, inaK, inaPb, inaQ, inaU, inaV, inaW, inaX, and inaZ found in and/or obtained from one or more of the following organisms: *Pseudomonas syringae*, Ps. *fluorescens* KUIN-1, *Erwinia herbicola, E. uredovora, Pantoea ananatis*, and *Xanthomonas campestris*. Other genes and/or organisms may also be used.

The fluidic analysis device can have first and second substrates attached together to define a microfluidic chip with at least one fluid transport channel and the fluid transport channel with a plurality of spaced apart freeze thaw valves.

The fluidic analysis device can be in fluid communication with a liquid buffer comprising the at least one INA. The at least one INA can be flowably introduced into a fluid port on the fluidic analysis device.

The at least one freeze thaw valve can be a plurality of spaced apart freeze thaw valves, each including a thermoelectric cooler in thermal communication with a defined region of the at least one fluid channel.

The at least one fluid channel can have at least a segment that is sized to be a microfluidic or nanofluidic channel.

The at least one fluid channel can have a primary transport channel and at least one reagent channel.

The fluidic analysis device can have a sample input, a buffer input and a bead well array, all in fluid communication with the primary transport channel. The at least one freeze thaw valve can be a plurality of spaced apart freeze thaw valves in fluid communication with the primary transport channel and/or at least one reagent channel.

The at least one fluid channel can include at least one fluid channel with the at least one INA bonded and/or coated to a surface thereof.

The fluid analysis device can have a bead storage/sample incubation chamber, a waste reservoir and a sample metering loop. The sample metering loop can reside between the bead storage/incubation chamber and the sample input.

The sample metering loop can have a volumetric capacity of between about 1 μL to about 1 mL and is in fluid communication with first and second freeze thaw valves on respective end portions of the sample metering loop. INAs can be used to improve freezing of the sample in the sample metering loop as a part of sample preparation including, but not limited to, cell lysis.

The at least one INA may comprise a structure similar to ice and/or a structure that aligns water molecules into an ice-like lattice.

Other embodiments are directed to methods of analyzing a target analyte. The methods include: providing a fluidic analysis device with at least one fluidic channel in fluid communication with at least one freeze thaw valve; introducing at least one ice nucleating agent (INA) into the at least one fluidic channel; and electronically selectively cooling the at least one freeze thaw valve to freeze the at least one freeze thaw valve using the at least one INA.

The at least one freeze thaw valve can be a plurality of spaced apart freeze thaw valves. The method can include (electronically) setting coolers thermally communicating with the at least one fluidic channel to a temperature, typically in a range of −100 degrees C. to −1 degree C., more typically between −50 degrees C. and −2 degrees C., to freeze the freeze thaw valves.

The fluidic device can be a fluidic microchip with a thickness between 0.01 mm and 10 mm.

The at least some of the freeze thaw valves have thermoelectric coolers set to a desired temperature, such as, for example, between about −50 degrees C. and about −2 degrees C., for a freeze operation that occurs in three minutes or less and the electronically selectively cooling can be carried out a plurality of times for a respective fluidic device, analyte and/or analysis.

The device can be a fluidic microchip.

The analyte can be or include a molecule of DNA, RNA, peptide, protein, glycan, pharmaceutical, or other biological or synthetic macromolecule or an elemental or inorganic compound.

The at least one INA can include an ice-nucleating protein, an ice-nucleating nucleic acid, ice-nucleating lipid, and/or an ice-nucleating carbohydrate.

The at least one INA can be extracted or derived from an organism.

The at least one INA can include an ice-nucleating protein (INP) and/or functional fragments thereof.

Optionally, the INP and/or functional fragment thereof is extracted from a membrane of *Pseudomonas syringae*.

The INP can be encoded by one or more of the following genes: iceE, iceH, inaA, inaE, inaF, inaK, inaPb, inaQ, inaU, inaV, inaW, inaX, and inaZ found in and/or obtained from one or more of the following organisms: *Pseudomonas syringae*, Ps. *fluorescens* KUIN-1, *Erwinia herbicola, E. uredovora, Pantoea ananatis*, and *Xanthomonas campestris*. Other genes and/or organisms may also be used.

The at least one INA is flowably introduced into the at least one fluidic channel in a liquid.

The liquid can be a buffer. The at least one INA can be diluted in the buffer.

The at least one INA can be introduced from a surface comprising a coating of the at least one INA and/or the at least one INA is adsorbed and/or chemically bonded to a surface of the at least one fluidic flow channel.

The at least one INA can have structure similar to ice and/or a structure that aligns water molecules into an ice-like lattice.

Yet other embodiments are directed to liquid buffers for DNA processing.

The liquid buffers can include at least one ice nucleating agent (INA), optionally diluted to between 1 molecule/μL and 10 billion molecules/μL. Concentrations of the INA can also exceed 10 billion molecules/μL and may span the nanomolar, micromolar, and/or millimolar concentration ranges.

The at least one INA can be extracted or derived from an organism.

The at least one INA can include an ice-nucleating protein (INPs) and/or a functional fragment thereof. Optionally, the INP and/or functional fragment thereof can be extracted from a membrane of *Pseudomonas syringae*.

The INP can be encoded by one or more of the following genes: iceE, iceH, inaA, inaE, inaF, inaK, inaPb, inaQ, inaU, inaV, inaW, inaX, and inaZ found in and/or obtained from one or more of the following organisms: *Pseudomonas syringae*, Ps. *fluorescens* KUIN-1, *Erwinia herbicola, E. uredovora, Pantoea ananatis*, and *Xanthomonas campestris*. Other genes and/or organisms may also be used.

The at least one INA can include one or more aptamers.

The at least one INA can include one or more of an ice-nucleating protein, an ice-nucleating nucleic acid, ice-nucleating lipid, and/or an ice-nucleating carbohydrate.

The at least one INA can have a structure similar to ice and/or a structure that aligns water molecules into an ice-like lattice.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 1A is a schematic end cutaway view of a microfluidic chip with at least one thermoelectric cooler positioned proximate a transport channel according to embodiments of the present invention.

FIG. 1B is a schematic top view of the device shown in FIG. 1A, illustrating the thermoelectric cooler below the substrate holding at least part of the transport channel according to embodiments of the present invention.

FIG. 2A is an enlarged top view of an exemplary microfluidic chip according to embodiments of the present invention.

FIG. 2B is an enlarged top view of the exemplary microfluidic chip shown in FIG. 2A and further illustrating additional components/features including exemplary freeze-thaw valve foot-prints according to embodiments of the present invention.

FIG. 5A is a digital photograph of a dual substrate microfluidic chip illustrating placement of a PTFE air-only membrane over a defined region of the chip according to embodiments of the present invention.

FIG. 5B is a digital photograph of an enlarged segment of the microfluidic chip shown in FIG. 5A but with the PTFE air-only membrane not in position over the bead storage/sample incubation chamber according to embodiments of the present invention.

DESCRIPTION OF EMBODIMENTS OF THE INVENTION

Figure 2C:
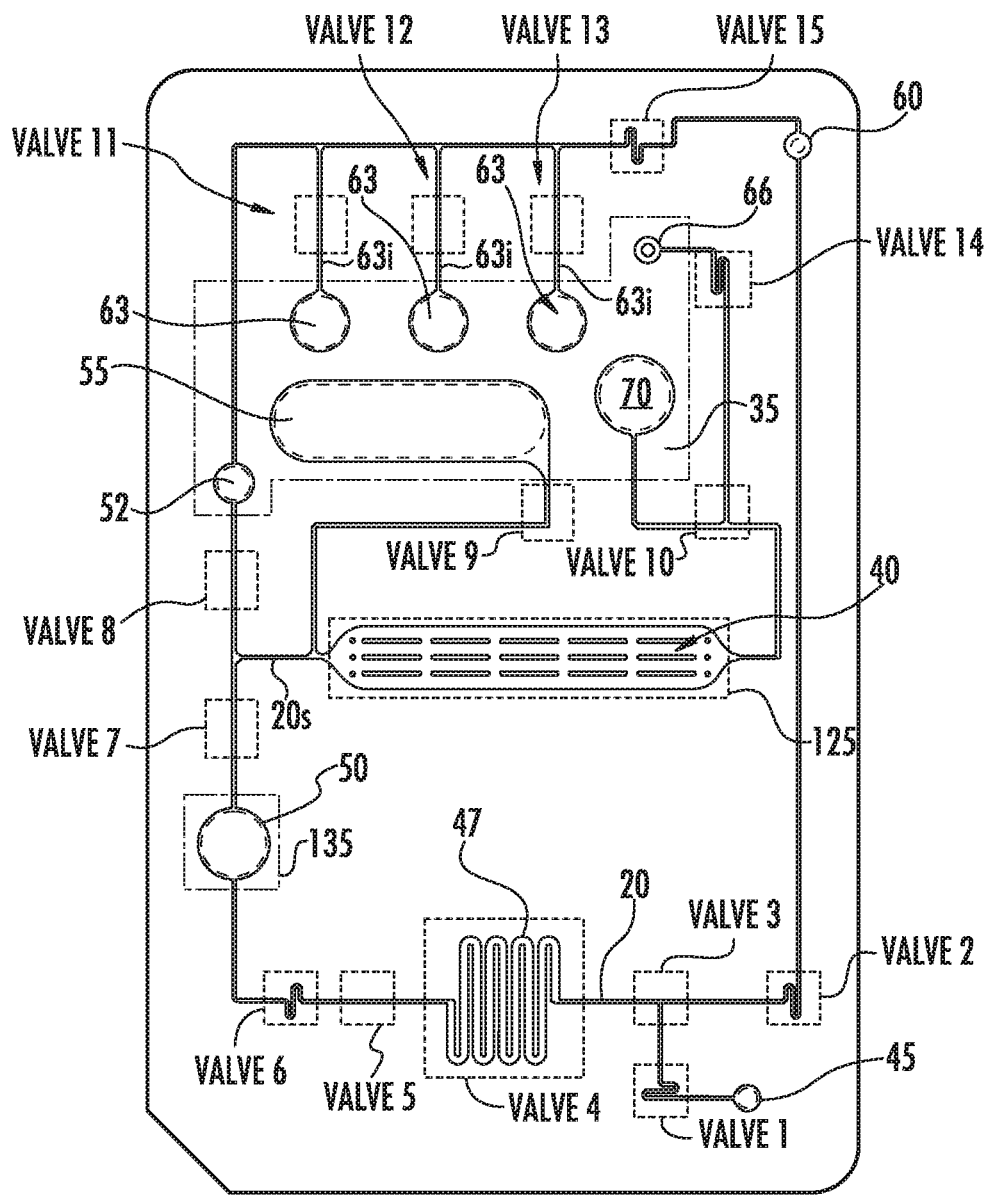
FIG. 2C is an enlarged top view of the microfluidic chip shown in FIG. 2B with annotations indicating valve numbers according to some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise. The abbreviations "FIG. and "Fig." for the word "Figure" can be used interchangeably in the text and figures.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. Well-known functions or constructions may not be described in detail for brevity and/or clarity.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

All of the document references (patents, patent applications and articles) are hereby incorporated by reference as if recited in full herein.

The terms "microchip" and "microfluidic chip" are used interchangeably and refer to a substantially planar, thin device. The microfluidic chip can be rigid, semi-rigid or flexible. The term "thin" refers to a thickness dimension that is 10 mm or less such as between 10 mm and 0.01 mm, and can be about 3 mm, about 2.5 mm, about 2 mm, about 1.5 mm, about 1 mm, about 0.5 mm, about 0.1 mm, and about 0.01 mm. The microchip typically has a width and length that is less than about 6 inches, more typically between about 1 inch and 6 inches. The microchip can have a width dimension that is less than a length dimension. The microfluidic chip can have a width dimension that is about 2.13 inches (54 mm) and a length dimension that is about 3.4 inches (85.5 mm), in some embodiments. The microchip can include micro-sized and/or nano-sized fluidic channels.

The term "primary dimension" refers to a width and/or depth dimension of a fluidic channel.

The terms "micro-sized" and "microfluidic" with respect to a fluidic channel refer to a fluid flow channel that has millimeter, sub-millimeter, or smaller size width and/or depth (e.g., the term includes millimeter, micrometer, and nanometer size channels) and includes channels with at least a segment having a width and/or depth in a size range of hundreds of microns or less, typically less than 900 microns and greater than 1 nm.

In some embodiments, the primary transport channel can be a microfluidic channel having a major length with at least one primary dimension that is between 1 nm to about 500 µm. The primary transport channel can, for example, have primary dimensions of about 250 m/250 µm (width/depth, i.e., width/height) dimensions. The term "primary fluid transport channel" refers to a fluidic channel, typically comprising at least a sub-length that is micro-sized channel or nanochannel through which an analyte flows for analysis.

The term "nanochannel" refers to a channel or trench having a critical dimension that is at a nanometer scale. The primary (also known as "critical") dimensions of a nanochannel are both typically below about 100 nm, including between about 1-70 nm. In some embodiments, at least one primary dimension can be about 5 nm or less (on average or at a maxima).

A fluidic channel has sidewalls and a floor. One or more fluidic transport channels can be formed into a solid substrate to have an open top surface and a closed bottom surface with the sidewalls extending therebetween. One or more top substrates, membranes or covers may be used to seal, cover or otherwise close the upper surface of the fluidic channel(s) and/or associated ports.

The term "about" refers to parameters that can vary between +/−20% or less, such as +/−10%.

The term "transverse" channel refers to a fluidic channel that crosses a respective fluid transport channel. A fluidic device can include a plurality of transverse channels that each merge into a primary transport channel.

The analyte in a sample can be any analyte of interest from a sample including, for example, various mixtures including synthetic and biological macromolecules, nanoparticles, small molecules, DNA, nucleic acids/polynucleic acids, peptides, proteins, glycans, pharmaceuticals, elemental compounds, inorganic compounds, organic compounds, and/or the like. The analyte can be one or more single analyte molecules. The sample or analyte of a sample can include one or more polar metabolites such as amino acids or charged molecules, molecules, peptides, and proteins. The sample and/or analyte may also or alternatively include molecules extracted from biofluids, blood, serum, urine, dried blood, cell growth media, lysed cells, beverages or food. The sample may also or alternatively include environmental samples such as water, air or soil.

The transport through the transport channel can be carried out using one or more of electrokinetics, concentration polarization and/or hydraulic or pneumatic pressure (forced pressure or pressure gradients), capillary forces or gravity.

An "ice-nucleating agent", "INA" or grammatical variations thereof, as used herein, refer to an agent that can and/or has the ability to catalyze and/or initiate ice crystal formation. Thus, an INA can and/or has the ability to nucleate ice. An INA may reduce the FTV actuation time at a given temperature. In some embodiments, the INA is a carbon-containing INA (i.e., contains at least one carbon atom). In some embodiments, an INA includes and/or is an ice-nucleating protein ("INP" in the singular, "INPs" in the plural) and/or a functional fragment thereof, an ice-nucleating nucleic acid, ice-nucleating lipid, and/or an ice-nucleating carbohydrate. In some embodiments, the INA is not a silver-containing agent, such as, for example, silver iodide and/or a nanoparticle comprising silver. In some embodiments, the INA does not cause and/or provide for the precipitation of a salt in a fluid in which it is present. In some embodiments, the INA does not interfere with a biological process and/or a process in an assay being studied and/or carried out using a microfluidic device. In some embodiments, the INA does not interfere with a component in the fluid in which is it present.

Accordingly, in some embodiments, an INA may be an organism, such as, for example, an invertebrate (e.g., a multicellular invertebrate), bacterium, fungi, and/or lichen, that includes and/or expresses an INP and/or a functional fragment thereof, an ice-nucleating nucleic acid, ice-nucleating lipid, and/or an ice-nucleating carbohydrate. In some embodiments, an INA may be obtained from an organism such as a bacterium and/or yeast that includes and/or expresses (e.g., by protein engineering) an INP and/or a functional fragment thereof, an ice-nucleating nucleic acid, ice-nucleating lipid, and/or an ice-nucleating carbohydrate. In some embodiments, an INA may be a component and/or derivative of an organism (e.g., a vertebrate and/or microorganism), such as, for example, a cell and/or cell component (e.g., a cell membrane) of the organism in which an INP and/or a fragment thereof, an ice-nucleating nucleic acid, ice-nucleating lipid, and/or an ice-nucleating carbohydrate is present. In some embodiments, nucleation effectiveness may be maximized when an INP and/or a functional fragment thereof remains in a cell membrane and/or is capable of interacting with other membrane components (e.g., other cell membrane proteins or lipids). In some embodiments, an ice-nucleating lipid may comprise all or a portion of a cell membrane, or may comprise all or a portion of a synthetic lipid membrane. An ice-nucleating lipid may enhance the effects of other ice-nucleating agents. In some embodiments, an INA may be an INP and/or a functional fragment thereof. In some embodiments, an INA may be an ice-nucleating nucleic acid, ice-nucleating lipid, and/or an ice-nucleating carbohydrate, such as, for example, a synthetic nucleic acid, a synthetic lipid, and/or synthetic carbohydrate that can nucleate ice. In some embodiments, an INA may be a naturally occurring, synthetic, or selectively evolved nucleic acid sequence.

Two or more (e.g., 3, 4, 5, 6, or more) different INAs may be present in a device, fluid channel, and/or FTV of the present invention. For example, a device of the present invention may comprise a plurality of FTVs and one FTV of the plurality of FTVs may include the same INA, the same combination of INAs, a different INA, and/or a different combination of INAs as another FTV of the plurality of FTVs. An INA may be present in a device, fluid channel, and/or FTV of the present invention in any suitable concentration. In some embodiments, an INA may be present in a device, fluid channel, and/or FTV at a concentration in a range of about 1 molecule or organism per L to about 10 billion molecules or organisms per µL or any range and/or individual value therein, such as, for example, about 1,000 molecules or organisms per L to about 3 million molecules or organisms per L. In some embodiments, the concentration of an INA can range from nanomolar to millimolar concentrations, such as, for example, from about 1 nM to about 1 mM. In some embodiments, an INA may be present in a device, fluid channel, and/or FTV at a concentration greater than 10 billion molecules/µL. In some embodiments, an INA may be present in a device, fluid channel, and/or FTV at a concentration in a range that spans the nanomolar, micromolar, and/or millimolar concentration range(s).

In some embodiments, an INA (e.g., an INP, an ice-nucleating nucleic acid, ice-nucleating lipid, and/or an ice-nucleating carbohydrate) comprises a structure (e.g., a secondary, tertiary, or quaternary structure or portion thereof) that can nucleate ice formation. In some embodiments, an INA (e.g., an aptamer, such as a DNA, RNA, and/or peptide aptamer) may comprise a structure similar to ice and/or may align water molecules into an ice-like lattice. In some embodiments, an INA may efficiently nucleate ice (i.e., the INA may not randomly nucleate ice like pollen and/or dust particles). In some embodiments, an INA may efficiently nucleate ice by freezing water and/or a solution at a given temperature in less time, on average, than the average time at which water and/or the solution freezes in the absence of the INA. In some embodiments, an INA may efficiently nucleate ice by freezing water and/or a solution in a respective freeze-thaw valve of a microfluidic device at a given temperature in less time with a standard deviation of less than 50 seconds (e.g., less than 45, 40, 35, 30, 25, 20, 15, 10, 5, 4, 3, 2 or 1 seconds) over successive freeze actuations, which can be assessed using ten trials, compared to the time at which water and/or the solution freeze in the freeze-thaw valve in the absence of the INA.

Example INAs include, but are not limited to, those described in U.S. Pat. Nos. 4,200,228; 4,706,463; 4,978,540; 5,233,412; 5,489,521; 5,532,160; 5,554,368; 5,620,729; 5,843,506; 5,972,686; 6,361,934; and 7,624,698 and European Patent Application No. 88114120.4, the portions of each of which are incorporated herein by reference in their entirety for the teachings relevant to this paragraph.

As used herein, the terms "polypeptide," "peptide" and "protein" refer to a polymer of amino acid residues. The terms encompass amino acid polymers in which one or more amino acid residue is an artificial chemical analogue of a corresponding naturally occurring amino acid, as well as to naturally occurring amino acid polymers.

The terms "nucleic acid," "nucleic acid molecule," "nucleotide sequence" and "polynucleotide" can be used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. A nucleic acid may comprise one or more non-naturally occurring nucleotides (e.g., an artificial chemical analogue of a naturally occurring nucleotide), which may or may not base pair in a manner similar to a naturally occurring nucleotide. In some embodiments, a nucleic acid may comprise one or more bases that do not normally occur in nature, and that may not necessarily base pair in a manner similar to naturally occurring nucleotides. The nucleic acid can be double-stranded or single-stranded. The term "nucleic acid," unless otherwise limited, encompasses analogues having the essential nature of natural nucleotide sequences in that they hybridize to single-stranded nucleic acids in a manner similar to naturally occurring nucleotides (e.g., peptide nucleic acids).

In some embodiments, an INP and/or a functional fragment thereof, an ice-nucleating nucleic acid, ice-nucleating lipid, and/or an ice-nucleating carbohydrate can confer the ice nucleation-active (Ice+) phenotype on an organism and/or cell in which it is present and/or expressed. The Ice+ phenotype as used herein refers to the ability of an organism and/or cell to catalyze and/or initiate ice crystal formation at relatively high temperatures, such as at temperatures below 0° C. and above −20° C. and/or any range and/or individual value therein. Thus, the Ice+ phenotype provides the organism and/or cell with the ability to produce ice nuclei at temperatures in a range of −20° C. to 0° C. As those of skill in the art will recognize, an INP and/or a functional fragment thereof (e.g., an INP and/or functional fragment thereof harvested and/or extracted from an organism in which it is expressed), ice-nucleating nucleic acid, ice-nucleating lipid, and/or ice-nucleating carbohydrate itself may have the ability to catalyze and/or initiate ice crystal formation.

In some embodiments, an INP may be a cell membrane protein, such as, for example, an outer cell membrane protein. An INP may be naturally expressed by and/or present in an organism, such as, for example, a vertebrate; invertebrate (e.g., a multicellular invertebrate); bacterium; fungi; and/or lichen. In some embodiments, an INP may be recombinantly expressed in an organism.

Example bacteria that naturally express an INP include, but are not limited to, *Pseudomonas syringae*, *P. antarctica*, *P. viridiflava*, *P. fluorescens*, *Erwinia herbicola*, *E. ananas*, and *Xanthomonas campestris*. In some embodiments, an INP may be present in an outer membrane of an organism (e.g., bacteria) that expresses the INP. In some embodiments, an INP may be harvested and/or extracted from a membrane of a bacterium that expresses the INP, such as, for example, *Pseudomonas syringae*.

As used herein with respect to polypeptides, the term "fragment" refers to a polypeptide that is reduced in length relative to a reference polypeptide (e.g., a full-length INP, such as naturally occurring INP) and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 300, 350, 400, 450, 500, or more consecutive amino acids. In some embodiments, the polypeptide fragment comprises, consists essentially of or consists of less than about 10, 15, 20, 25, 30, 35, 40, 45, 50, 55, 60, 65, 70, 75, 80, 85, 90, 95, 100, 125, 150, 175, 200, 225, 250, 300, 350, 400, 450 or 500 consecutive amino acids.

As used herein with respect to polypeptides, the term "functional fragment" refers to a polypeptide fragment that retains at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5% or more of at least one biological activity of the full-length polypeptide (e.g., the ability to catalyze ice formation and/or confer the ice nucleation-active (Ice+) phenotype). In some embodiments, the functional fragment may have a higher level of at least one biological activity of the full-length polypeptide. In some embodiments, an organism containing a functional fragment of an INP (e.g., a bacterium containing an INP functional fragment) may have a higher level of at least one biological activity of the full-length polypeptide.

In some embodiments, an INP and/or a functional fragment thereof may comprise at least 1 repeat of two or more consecutive amino acids, such as, for example, a repeat of an 8, 16, and/or 48 amino acid sequence. In some embodiments, the two or more consecutive amino acids (e.g., the 8, 16, and/or 48 amino acid sequence) may be repeated 1, 2, 3, 4, 5, 6, 7, 8, 9, or more times in the INP and/or functional fragment. The two or more consecutive amino acids (e.g., the 8, 16, and/or 48 amino acid sequence) may be consecutively repeated 1, 2, 3, 4, 5, 6, 7, 8, 9, or more times in the INP and/or functional fragment. In some embodiments, the repeating sequence can be imperfect and/or exhibit a natural variation. Example amino acid sequences include, but are not limited to, those described in Green & Warren, Nature 1985, vol. 317, pp 645-648, the contents of which are incorporated herein by reference for the portions relevant to this paragraph. In some embodiments, an INP and/or a functional fragment thereof may comprise a tandemly repeated 8, 16, and/or 48 amino acid sequence, which may be present in the internal region of an INP.

In some embodiments, an INP can be encoded by one or more genes, such as, for example, but not limited to, iceE, iceH, inaA, inaE, inaF, inaK, inaPb, inaQ, inaU, inaV, inaW, inaX, and/or inaZ. An INP may be present or found in and/or obtained from an organism, such as, for example, but not limited to, *Pseudomonas syringae*, Ps. *fluorescens* KUIN-1, *Erwinia herbicola*, *E. uredovora*, *Pantoea ananatis*, *Xanthomonas campestris*, *E. carotovora*, Ps. *antarctica*, Ps. *aeruginosa*, Ps. *putida*, Ps. *viridiflava*, Pa. *agglomerans*, *E. ananas*, and/or Ps. *borealis*. In some embodiments, an INP may be encoded by a gene present or found in and/or obtained from an organism as shown in Table 1. For example, the INP may be a polypeptide encoded by the iceE gene found or present in and/or obtained from *Erwinia herbicola*.

TABLE 1

Example ice-nucleating genes/proteins and the species from which they may be found or present in and/or obtained from.

| Ice-nucleating gene/protein | Species |
| --- | --- |
| iceE | *Erwinia herbicola* |
| iceH | *E. herbicola* |
| inaA | *Pantoea ananatis, E. ananas* |
| inaE | *E. herbicola* |
| inaF | *Pseudomonas fluorescens* KUIN-1 |
| inaK | *Ps. syringae* |
| inaPb | *Ps. borealis* |
| inaQ | *Ps. syringae* |
| inaU | *Pa. ananatis, E. uredovora* |
| inaV | *Ps. syringae* |
| inaW | *Ps. fluorescens* |
| inaX | *Xanthomonas campestris* |
| inaZ | *Ps. syringae* |

In some embodiments, an INP and/or a functional fragment thereof may be a polypeptide encoded by the inaZ gene, such as, for example, a polypeptide as set forth in Accession No. P06620 (ICEN_PSESY). The central domain of an INP (e.g., inaZ) may comprise 122 imperfect repeats of an octapeptide, and it may have a structure similar to that of ice. In some embodiments, an INP and/or a functional fragment thereof may align water molecules into an ice-like lattice. In some embodiments, an INP and/or a functional fragment thereof may have a structure comprising at least one beta hairpin (e.g., 1, 2, 3, 4, 5, or more), and optionally at least one beta hairpin may comprise 1, 2, or more octapeptide repeat(s). In some embodiments, an ice-nucleating nucleic acid, ice-nucleating lipid, and/or an ice-nucleating carbohydrate may have a structure similar to at least part of a structure of an INP.

In some embodiments, an INP and/or functional fragment thereof may be naturally, synthetically, and/or recombinantly obtained and/or produced. In some embodiments, an INP and/or functional fragment thereof may be isolated, obtained, harvested, and/or extracted from an organism in which it may naturally and/or recombinantly be expressed. In some embodiments, an INP and/or functional fragment thereof may be isolated, obtained, harvested, and/or extracted from an organism or microorganism (e.g., bacteria, fungi, etc.) and used as an INA.

In some embodiments, an INP and/or functional fragment thereof may be obtained through recombinant techniques and may be based on plasmids from natural and/or synthetic DNA. A recombinant INP and/or functional fragment thereof may be expressed in an organism such as a bacterium (e.g., *Escherichia coli*) and/or a yeast (e.g., *Saccharomyces cerevisiae*). Similarly, the INP agent can be expressed in other suitable organisms such as plants or animals. A recombinant INP and/or functional fragment thereof may be modified to aid in the expression, purification, modification, and/or stability of the INP and/or functional fragment. For example, a recombinant INP and/or functional fragment thereof may be modified to include a polyhistidine tag to facilitate purification of the polypeptide from an organism in which it is expressed and/or may be modified to have more preferable characteristics, such as, for example, improved resistance to denaturation under different conditions such as a range of temperatures, pH levels, ionic strengths, and solvent strengths. A recombinant INP and/or functional fragment thereof may be modified to include a functional group for attachment to a surface or another molecule. In some embodiments, a recombinant INP and/or functional fragment thereof may be modified to improve ice nucleation. For example, recombinant INP and/or functional fragment thereof may be modified to include a repeating the sequence to link two or more INPs/functional domains together, to link phospholipids during PTMs, or to include spacers to optimize the distance between INP domains. In some embodiments, a recombinant INP and/or functional fragment thereof may be modified to group two or more INPs and/or functional fragments thereof together.

In some embodiments, an INP and/or functional fragment thereof, ice-nucleating nucleic acid, ice-nucleating lipid, and/or ice-nucleating carbohydrate may be isolated. As used herein with respect to polypeptides, nucleic acids, lipids, and/or carbohydrates, the term "isolated" refers to a polypeptide, nucleic acid, lipid, and/or carbohydrate that, by the hand of man, exists apart from its native environment and is therefore not a product of nature. In some embodiments, the ice-nucleating polypeptide, ice-nucleating nucleic acid, ice-nucleating lipid, and/or ice-nucleating carbohydrate exist in a purified form that is substantially free of cellular material, viral material, culture medium (when produced by recombinant DNA techniques), or chemical precursors or other chemicals (when chemically synthesized). An "isolated fragment" is a fragment of a polypeptide, nucleic acid, lipid, and/or carbohydrate that is not naturally occurring in a substantial concentration as a fragment and would not be found in the natural state above trace levels. "Isolated" does not mean that the preparation is technically pure (homogeneous), but rather that it is sufficiently pure to provide the ice-nucleating polypeptide, ice-nucleating nucleic acid, ice-nucleating lipid, and/or ice-nucleating carbohydrate in a form in which it can be used for the intended purpose. In certain embodiments, a composition comprising an ice-nucleating polypeptide, ice-nucleating nucleic acid, ice-nucleating lipid, and/or ice-nucleating carbohydrate is at least about 50%, 55%, 60%, 65%, 70%, 75%, 80%, 85%, 90%, 95%, 96%, 97%, 98%, or 99% or more pure.

In some embodiments, an INA may nucleate ice crystals on a microfluidic scale. Thus, an INA as described herein may catalyze and/or initiate ice crystal formation in water and/or a solution (e.g., an aqueous solution) on a microfluidic scale, such as, for example, in a microfluidic chip, to thereby freeze the water and/or solution. The volume of fluid (e.g., water) that may freeze in a microfluidic chip (e.g., in a fluidic channel and/or FTV) may be in a range of about 1 femtoliter to about 100 microliters and/or any range and/or individual value therein. In some embodiments, a larger fluid volume that can freeze in one or more freeze-thaw valves may be used, such as about 1 milliliter or a plurality of milliliters. "Freeze" as used herein refers to the formation of a solid phase in an amount sufficient to block and/or stop the flow of a fluid present in a FTV on a microfluidic device associated with an external cooling source, such as a thermoelectric cooler. Thus, after freezing, the solid phase in the microfluidic chip (e.g., in a fluidic channel and/or FTV) may have a volume greater than that of the fluid prior to freezing.

In some embodiments, the use of an INA in a microfluidic chip may freeze water and/or a solution at a higher temperature and/or in less time, on average, than the temperature and/or time at which water and/or the solution freeze in the absence of the INA. In some embodiments, an INA may freeze water and/or a solution at a temperature that is at least 5° C. higher (e.g., 6, 7, 8, 9, 10° C., or more) than the temperature at which water and/or the solution freeze in a given amount of time in the absence of the INA. In some embodiments, an INA may reduce the average time water and/or a solution is held below its melting point (e.g., 0° C. for water) before crystallization occurs. In some embodiments, an INA may reduce the average time water and/or a solution is held below its melting point (e.g., 0° C. for water) before crystallization occurs by at least about 5% or more, such as, for example, by at least 10%, 15%, 20%, 25%, 50%, or more.

An INA may catalyze and/or initiate ice crystal formation in water and/or a solution (e.g., an aqueous solution) at a temperature below 0° C. and above −50° C. and/or any range and/or individual value therein, such as, for example, about −1° C. to about −20° C., about −6° C. to about −14° C., about −2° C. to about −12° C., about −1° C. to about −30° C., about −2° C. to about −8° C., about −2° C. to about −50° C., or about −5° C. to about −25° C. In certain embodiments, an INA may catalyze and/or initiate ice crystal formation in water and/or a solution at a temperature of about 0, −1, −2, −3, −4, −5, −6, −7, −8, −9, −10, −11, −12, −13, −14, −15, −16, −17, −18, −19, −20, −21, −22, −23, −24, −25, −26, −27, −28, −29, −30, −31, −32, −33, −34, −35, −36, −37, −38, −39, −40, −41, −42, −43, −44, −45, −46, −47, −48, −49 or −50° C. and/or any range and/or individual value therein. The freeze/thaw temperatures can be measured in a microfluidic transport channel holding a solution with the INA at a desired freeze-thaw region. The actual temperature (setting) of a thermo-electric source providing the freeze and/or thaw input will typically be different than the temperature in the transport channel at the freeze/thaw region, e.g., a freeze temperature setting such as −45° C. to −20° C., will result in a freeze temperature in the material containing the INA in the transport channel that is above the setting, typically by about 5 to 25° C. above the setting.

One, and typically all, respective FTVs 22 can operate at a freeze time of less than three minutes, typically under about 45 seconds, more typically between 2 seconds and 33 seconds. Thaw times for one or more FTVs 22 can be less than corresponding freeze times, typically between 1-30 seconds, such as between 1-15 seconds.

An INA may be designed to function in water and/or a solution, such as an aqueous solution, and may not need to be dry. An INA may be provided in a number of ways. In some embodiments, an INA may be diluted into a buffer for input into and/or onto a microfluidic chip. In some embodiments, an INA may be provided in a buffer or other liquid suitable for use with immunoassays (e.g., a Tris-based or phosphate-based buffer). Other formulations/delivery mechanisms of the INPs are described below.

The term "circuit" refers to an entirely hardware embodiment or an embodiment combining software and hardware.

The term "homogenous nucleation" refers to when small aggregates of a solid-like phase (embryos) exist throughout the liquid phase, the embryos reach a critical size, and the embryos trigger continued growth of the solid phase. A homogeneous nucleation generally occurs at about −37° C. or below for water.

The term "heterogeneous nucleation" refers to a phase transition from a metastable supercooled state to a stable solid state due to the presence of foreign substance (e.g., an INA) in the liquid phase. Heterogeneous nucleation typically occurs at nucleation sites on a surface of a liquid and, for water, generally occurs at a temperature in a range of about 0° C. and above −40° C. In some embodiments, an INA may heterogeneously nucleate a solution and/or liquid in which it is present.

The term "oligonucleotide" refers to a nucleic acid sequence of about five nucleotides to about 500 nucleotides (e.g. 5, 6, 7, 8, 9, 10, 12, 15, 18, 20, 21, 22, 25, 30, 35, 40, 45, 50, 55, 60, 65, 70, 75, 80, 85, 90, 100, 125, 150, 175, 200, 250, 300, 350, 400, 450 or 500 nucleotides). In some embodiments, for example, an oligonucleotide can be from about 15 nucleotides to about 40 nucleotides, or about 20 nucleotides to about 25 or to about 30 nucleotides, which can be used, for example, as a primer in a polymerase chain reaction (PCR) amplification assay and/or as a probe in a hybridization assay or in a microarray. Oligonucleotides for processing can be natural or synthetic, e.g., DNA, RNA, PNA, LNA, modified backbones, etc., or any combination thereof as are well known in the art.

Probes and primers, including those for either amplification and/or detection, are oligonucleotides (including naturally occurring oligonucleotides such as DNA and synthetic and/or modified oligonucleotides) of any suitable length, but are typically from 5, 6, or 8 nucleotides in length up to 40, 50 or 60 nucleotides in length, or more. Such probes and or primers may be immobilized on or coupled to a solid support such as a bead, chip, pin, or microtiter plate well, and/or coupled to or labeled with a detectable group such as a fluorescent compound, a chemiluminescent compound, a radioactive element, or an enzyme.

In some embodiments, an INA may be immobilized on, attached to, or coupled to a solid support, such as, e.g., a particle or a bead. An INA may be immobilized on, attached to, or coupled to a solid support prior to being introduced into a fluidic analysis device. The INA immobilized on, attached to, or coupled to the solid support may be introduced into at least one fluidic channel of a fluidic analysis device and/or may be used to freeze and thaw at least one freeze thaw valve of the fluidic analysis device.

In some particular embodiments, fluidic devices with freeze-thaw valves and comprising INAs (e.g., an INP and/or functional fragment thereof and/or a microorganism comprising the same) can carry out PCR in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps can be cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. The amplified sequence can also be detected by an intercalating dye in the reaction mixture and monitoring the fluorescence signal strength, which will be proportional to the total mass of double stranded DNA. Although embodiments according to the present invention are described with respect to PCR reactions, it should be understood that other nucleic acid amplification methods can be used, such as reverse transcription PCR (RT-PCR) including isothermal amplification techniques such as rolling circle amplification or loop-mediated isothermal amplification (LAMP).

DNA amplification techniques such as the foregoing can involve the use of a probe, a pair of probes, or two pairs of probes which specifically bind to DNA containing a polymorphism or mutation of interest, but do not bind to DNA that does not contain the polymorphism of interest under the same hybridization conditions, and which serve as the primer or primers for the amplification of the DNA or a portion thereof in the amplification reaction. Such probes are sometimes referred to as amplification probes or primers herein.

The term "reagent" refers to any substance or compound, including primers, a nucleic acid template and/or an amplification enzyme(s) that is added to a system in order to bring about a chemical reaction, or added to see if a reaction occurs. Amplification reagents or reagent refer to those reagents (deoxyribonucleotide triphosphates, buffer, etc.) generally used for amplification except for primers, nucleic acid template and the amplification enzyme. Typically, amplification reagents along with other reaction components are placed and contained in a reaction vessel (test tube, microwell, etc.).

The term "magnetic" as used herein includes ferromagnetic, paramagnetic and super paramagnetic properties.

In some embodiments, the fluidic devices contemplated by embodiments of the invention may employ an oligonucleotide probe which is used to detect DNA containing a polymorphism or mutation of interest and is an oligonucleotide probe which binds to DNA encoding that mutation or polymorphism, but does not bind to DNA that does not contain the mutation or polymorphism under the same hybridization conditions. The oligonucleotide probe can be labeled with a suitable detectable group, such as those set forth below. Such probes are sometimes referred to as detection probes or primers herein.

Although embodiments according to the present invention are described herein with respect to PCR reactions, it should be understood that the microfluidic devices and methods described herein may be used in various other processes, e.g., reactions. For example, any nucleic acid transcription and/or amplification-related reaction is within the scope of the current invention, including but not limited to PCR reactions, real-time PCR (rt-PCR), digital PCR (dPCR), reverse transcription of RNA into cDNA (RT), PCR of cDNA from previous RT step (RT-PCR), RT-PCR using real-time or digital quantification, immuno-PCR (iPCR) and its variants, loop-mediated isothermal amplification (LAMP), rolling circle replication, and/or non-enzymatic nucleic acid amplification methods (e.g., "DNA circuits"). Methods of sequencing nucleic acids including next generation sequencing methods including sequencing by synthesis or hybridization-based methods are also included within the scope of the invention. Other reactions that are included within the scope of the present invention include but are not limited to enzyme-linked immunosorbent assays (ELISA), single molecule array (SiMoA) or digital ELISAs, reactions in which multiple beads are used to deliver different reagents for combinatorial chemistry, reactions where the beads deliver a catalyst reagent, and/or reactions where "click" chemistry reagents are delivered in stoichiometries determined by stochastic bead loading. See, e.g., U.S. Ser. No. 14/402,565, for examples of processes using cleaved reagents, the contents of which are hereby incorporated by reference as if recited in full herein.

Turning now to the figures, by way of simple illustration, one example of a fluidic device contemplated by embodiments of the invention can include a microfluidic chip 10 as shown in FIGS. 1A and 1B. The microfluidic chip 10 has at least one fluid transport channel 20. Some embodiments can comprise a plurality of transport channels. A respective transport channel 20 has at least one defined flow region 20r with a freeze thaw "valve" 22. The freeze thaw valve 22 is in thermal communication with at least one cooler 25; typically, the fluidic device comprises a plurality of freeze thaw valves 22, each with a respective cooler 25, optionally one or more thermoelectric cooler (TEC) 25t, that can be used to both freeze and thaw liquid in respective defined regions of a transport channel 20. The at least one thermoelectric cooler 25t can be, for example, a Peltier cooler.

In some embodiments, one or more of the FTVs 22 can include a plurality of coolers 25, such as one over and one under a corresponding channel segment 20r associated with a respective FTV 22, which may increase a freeze action, i.e., shorten a time to freeze.

In some particular embodiments, the thermoelectric cooler 25t can be configured as a solid-state device composed of n- and p-type semiconductors sandwiched between thin sheets of electrically insulating yet thermally conductive material. When direct current is applied to the array of n- and p-type elements, one side of the device cools due to the Peltier effect and absorbs heat from the surrounding environment. The heat is transported through the device to the opposite side and released, creating a temperature gradient between the two sides of the TEC. See, e.g., Sgro et al., *Thermoelectric Manipulation of Aqueous Droplets in Microfluidic Devices*, Anal Chem. 2007, 79(13): 4845-4851, the contents of which are hereby incorporated by reference as if recited in full herein. Microscale and larger TECs can be embedded in, integrally attached to and/or releasably attached directly or indirectly, to a microfluidic chip 10 for localized cooling of nanoliter and/or microliter sized volumes. For other examples of thermoelectric coolers, see, e.g., Maltezos et al., *Thermal management in microfluidics using micro-Peltier junctions*, Applied Phys. Lett. 87, 154105 (2005), the contents of which are hereby incorporated by reference as if recited in full herein.

The cooler 25 can have a thermal footprint "F" in thermal communication with the microfluidic chip 10 that can have a length L measured in a flow direction toward and/or along the transport channel 20, some footprints F of FTV regions 22 can be larger (width and/or length) than others (FIGS. 2B, 2C, 3B, 3C, for example). In some particular embodiments, the footprint F can be defined by the size of a respective TEC 25t. For example, the TEC 25t can have a surface area of about 16 mm², e.g., have a width and length dimension of about 4 mm by 4 mm, for at least some of the FTV regions 22.

FIGS. 2A-2C and 3A-3C illustrate examples of microfluidic chips 10, each with a plurality of freeze thaw valves 22 in thermal contact with respective coolers 25, bead well array 40, a sample input 45, a bead storage/sample incubation chamber 50 and a waste reservoir 55. A sample metering loop 47 can reside between the bead storage/incubation chamber 50 and the sample input 45. The sample metering loop 47 can optionally have a serpentine shape as shown. The sample metering loop 47 may have a volumetric capacity of between about 1 μL to about 1 mL, more typically between 1 and 500 μL, such as between about 10.75 μL and 29 μL, in some embodiments. The loop 47 can have opposing open ends merging into the primary fluid transport channel 20.

Figures 3A, 3B:
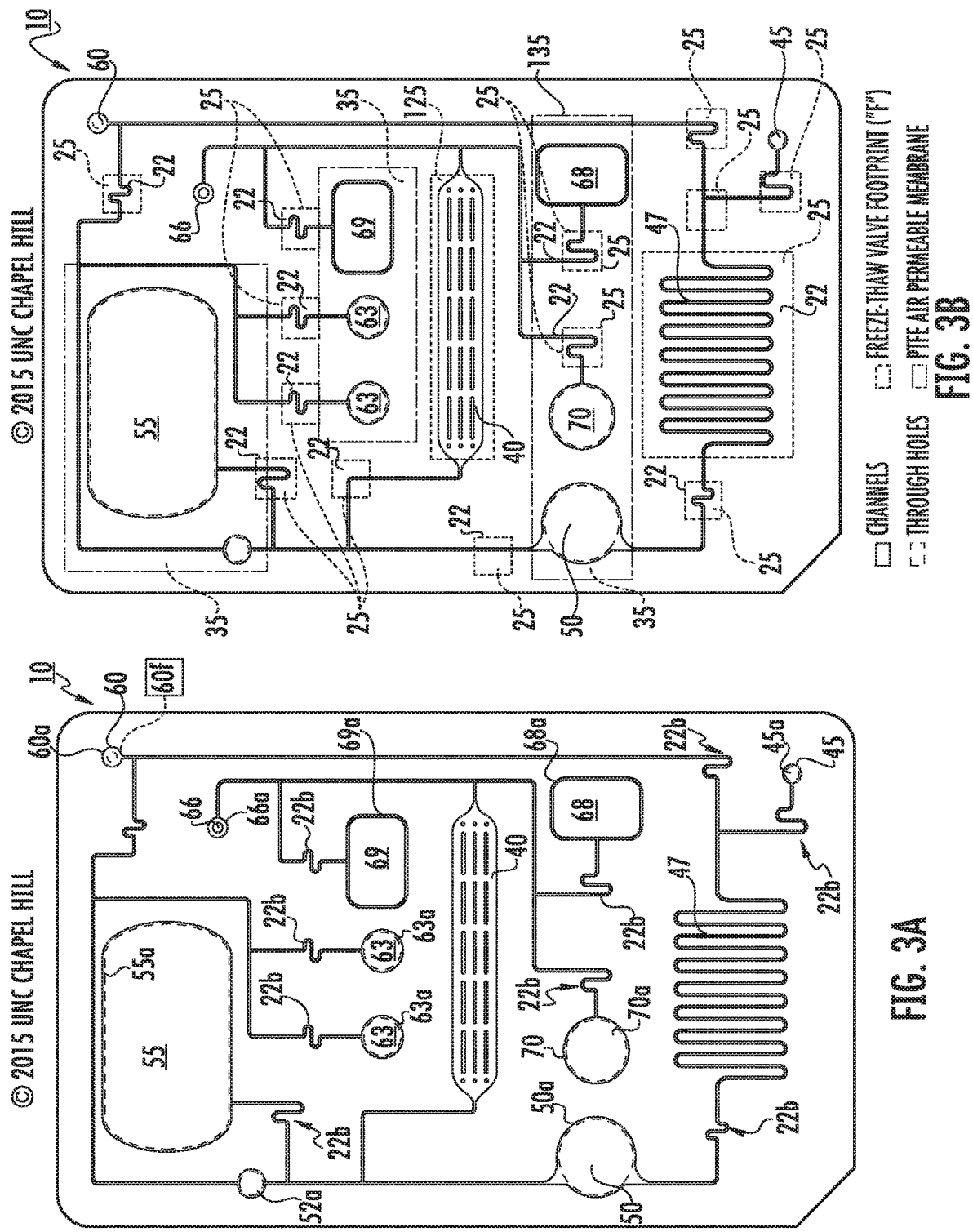
FIG. 3A is an enlarged top view of an exemplary microfluidic chip according to embodiments of the present invention.
FIG. 3B is an enlarged top view of the exemplary microfluidic chip shown in FIG. 3A and further illustrating additional components/features including exemplary freeze-thaw valve foot-prints according to embodiments of the present invention.

As shown, for example, in FIGS. 2A and 3A, some of the fluidic channel segments associated with freeze-thaw valves 22 can have curvilinear elbows 22b that can be sized and configured to increase volume cooled by a cooler to facilitate a freezing action.

The bead well array 40 can have a temperature control member 125 residing under or above the well array 40 over its entire length or substantially over its entire length, potentially terminating adjacent, before or after the inlet/outlet necks thereof.

The microfluidic chip 10 and/or one layer of the chip 10 can have through-holes (i.e., access apertures and/or ports) and/or fluid paths extending through one or both sides of the chip 10 at defined locations for fluid intake/exit regions.

As shown in FIGS. 2A and 3A, the sample input 45 can include a sample input through an access aperture or via 45a. The bead storage/sample incubation chamber 50 can include an access via or aperture 50a. The bead washing and secondary reagent incubation chamber 52 can include an access aperture or via 52a. The buffer input 60 can include an access via or aperture 60a (FIG. 3A). The sealing agent input 66 can include an access aperture or via 66a. The detection substrate (and/or PCR master mix) 70 can include an access aperture or via 70a. The waste reservoir 55 can include a through-hole through one side or via 55a. The secondary reagent inputs 63 can include access apertures or vias 63a.

FIG. 3A illustrates the microfluidic chip 10 can include an array pre-treat reagent chamber 68 with a through hole or via 68a and an array wash and oil purge waste chamber 69 with a through hole or via 69a.

Figure 3C:
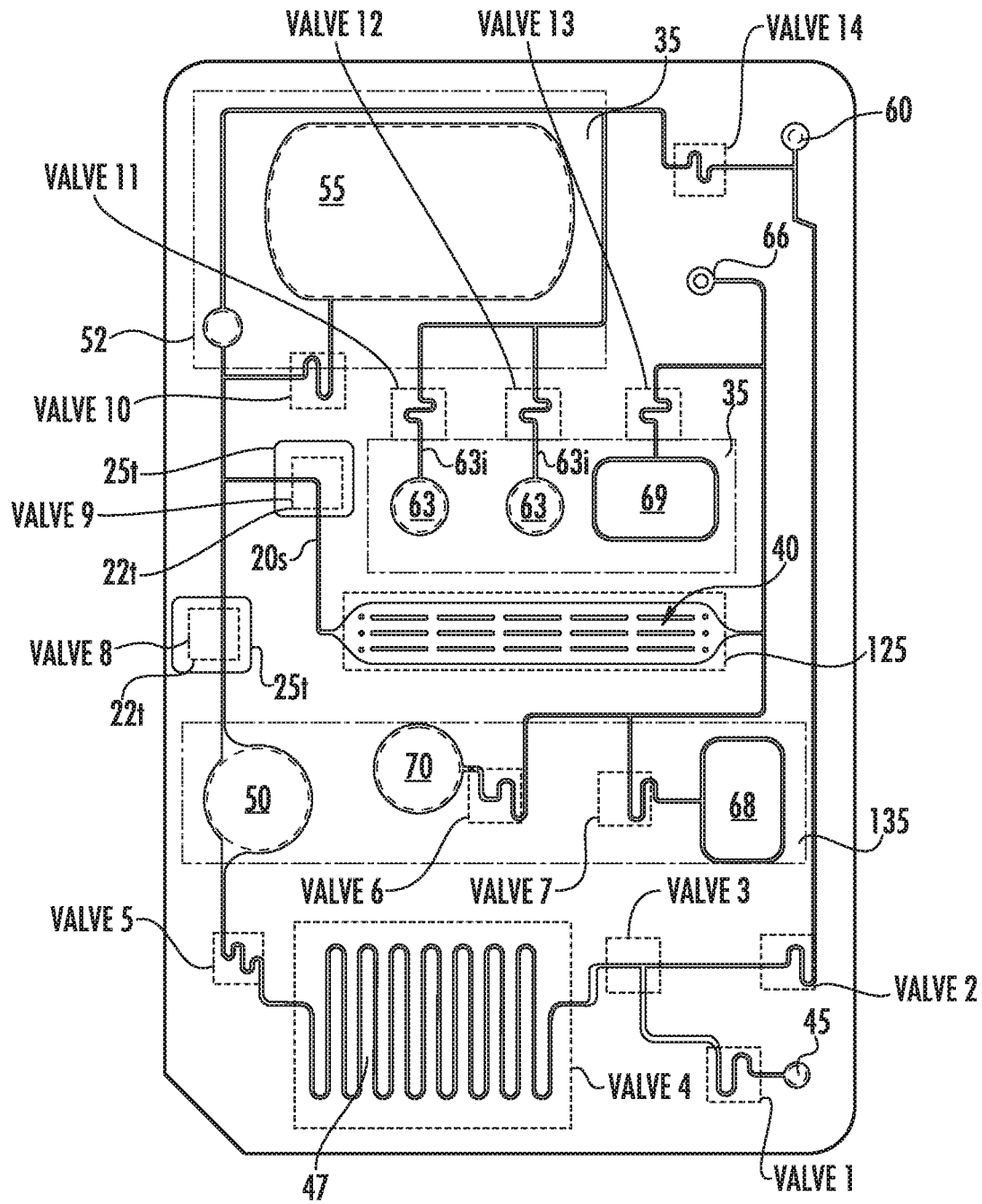
FIG. 3C is an enlarged top view of the microfluidic chip shown in FIG. 3B with annotations indicating valve numbers according to some embodiments of the present invention.

FIGS. 2A-2C illustrate fifteen freeze thaw valves 22 with coolers 25 and FIGS. 3A-3C illustrate fourteen freeze thaw valves 22 with coolers 25 (e.g., TEC members/elements 25t), some on a top surface 10t (FIG. 4) of the microfluidic chip 10 and a plurality under the bottom 10b of the microfluidic chip 10.

As shown in FIG. 2C, coolers 25 (e.g., TEC members 25t) for freeze thaw valves 22 can be positioned on each side of a channel segment 20s leading to the bead well array 40, e.g., valves 7 and 8, valve 7 being upstream of and adjacent the bead storage/incubation chamber 50, can reside on the top side of the fluidic chip 10 and the remainder can reside under the microfluidic chip 10. As shown in FIG. 3C, coolers 25 for freeze-thaw valves 8 and 9 can reside on top of the microfluidic chip 10, one upstream of and adjacent the bead storage/incubation chamber 50 and one inside the channel segment 20s leading to the bead well array 40.

The top side coolers 25 for the freeze-thaw valves 22 (i.e., valves 7/8, FIG. 2C, valves 8/9, FIG. 3C) can reside in a thin region, e.g., a region that is about 30-95% the thickness of the top substrate 10t and/or primary body of the chip itself, e.g., about a 900 μm thick region on a top of the substrate that has a nominal or average thickness of between 1-2 mm outside this area/volume. That is, the microfluidic chip 10 can have a top substrate 10t (FIGS. 4A, 4B) that is molded and holds the fluidic channels 20, 63i, 20s, for example. The thinner regions 22t can be sized and configured to hold and/or be in thermal communication with the top-mounted coolers 25t.

Figure 7:
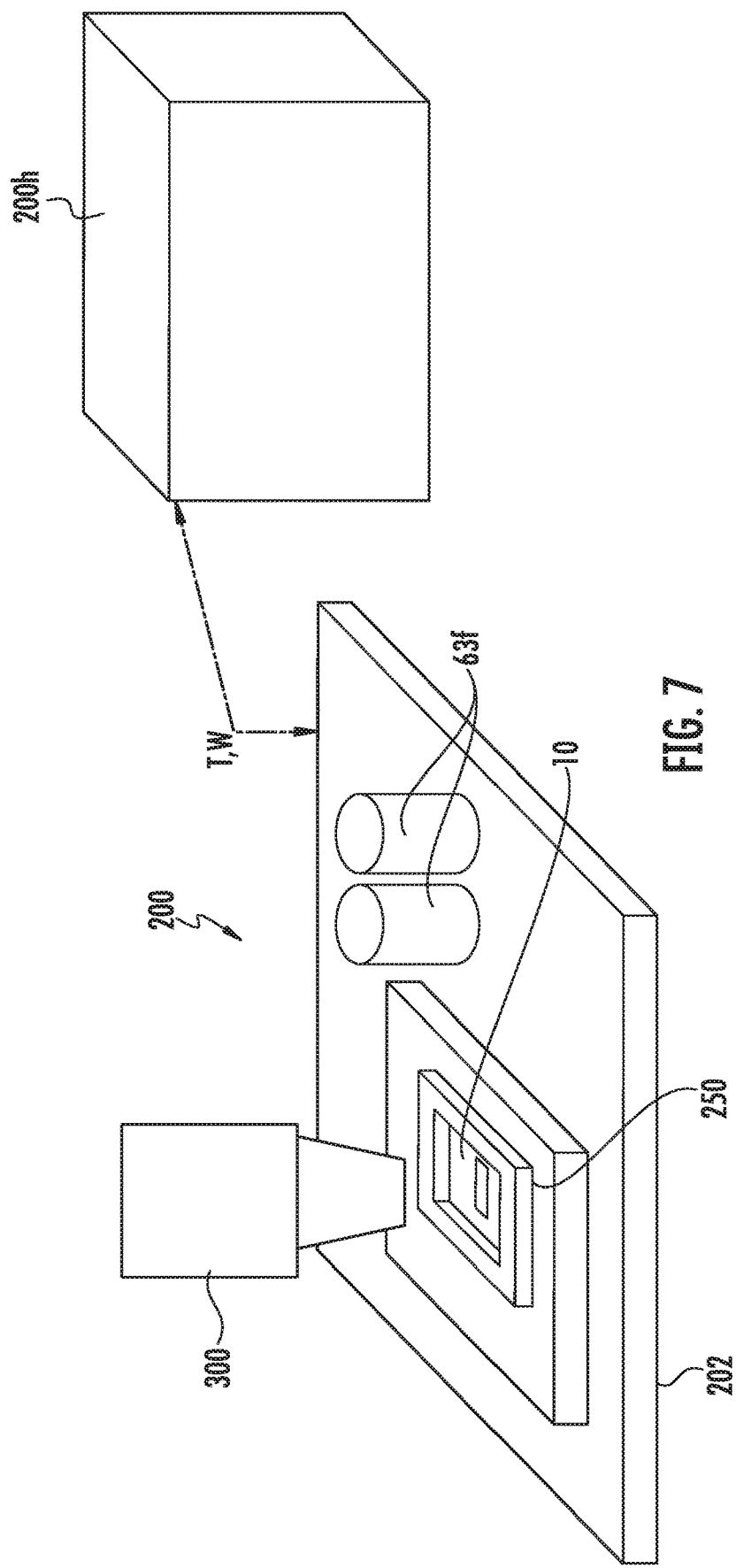
FIG. 7 is a side, front perspective view of a portion of an automated test system that can releasably engage one or more microfluidic chips for analysis according to embodiments of the present invention.

The microfluidic chip 10 can include a buffer input 60 and a plurality of reagent inputs 63 (e.g., fluid reservoirs 63f, FIG. 7). FIGS. 2A-2C illustrate three secondary reagent inputs 63 while FIGS. 3A-3C illustrate two secondary reagent inputs 63. The reagent inputs 63 can each be associated with an input channel 63i having a corresponding freeze thaw valve 22 with a cooler 25.

The microfluidic chip 10 can include a bead washing/secondary incubation chamber 52 in fluid communication with one or all of the secondary reagent inputs 63.

The microfluidic chip 10 can also include a detection substrate region and/or a PCR master mix region 70. Where used, the PCR master mix can comprise a premixed, ready-to-use solution containing a thermostable DNA polymerase, dNTPs, $MgCl_2$ and reaction buffers at optimal concentrations for efficient amplification of DNA templates by PCR, for example.

The microfluidic chip 10 can include a sealing agent input 66. The sealing agent can comprise mineral, silicone, hydrocarbon, fluorocarbon-based, a mixture of such oils, or a multiply-functionalized synthetic oil and/or waxes.

FIGS. 2B, 2C, 3B and 3C illustrate exemplary footprints F of freeze-thaw valves 22 associated with a cooler 25, illustrated by a closed perimeter drawn about respective defined localized regions of fluidic channels. These figures also illustrate air permeable membranes 35, 135. FIGS. 2B and 2C illustrate one membrane 35 over the reagent inputs 63, bead washing and secondary reagent incubation chamber 52 and another membrane 135 over the bead storage and sample incubation chamber 50. FIGS. 3B and 3C illustrate two discrete spaced membranes 35 covering the waste reservoir 55 and the reagent inputs 63, respectively. Another air-permeable membrane 135 resides over the bead storage/incubation chamber 50 and adjacent detection substrate and/or PCR master mix 70 and array pre-treat reagent 68.

Figure 4B:
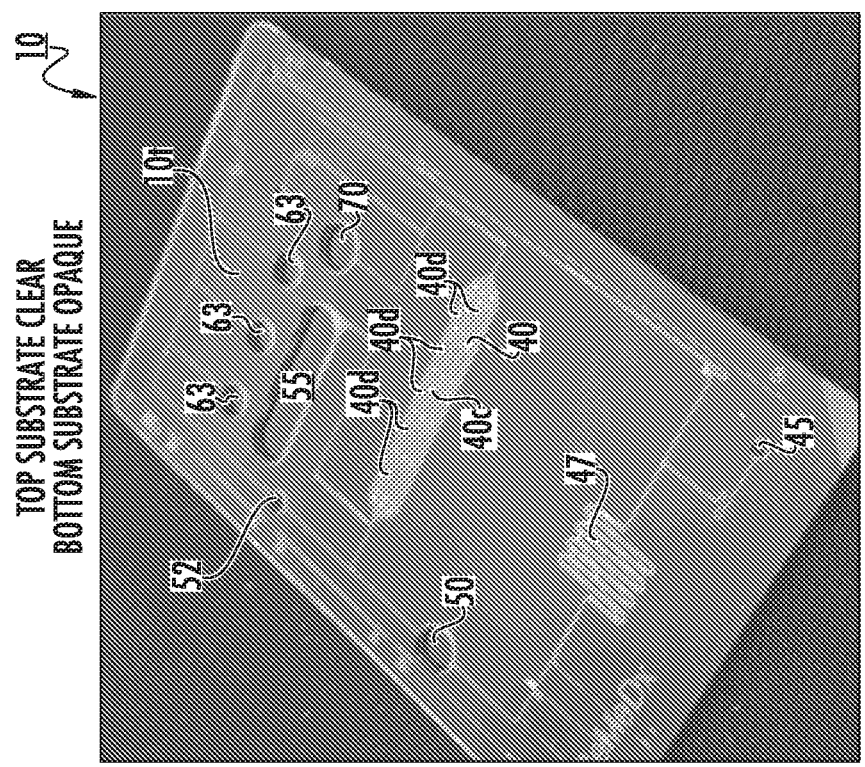
FIG. 4B is a digital photograph of a dual substrate microfluidic chip according to other embodiments of the present invention.
Figure 4A:
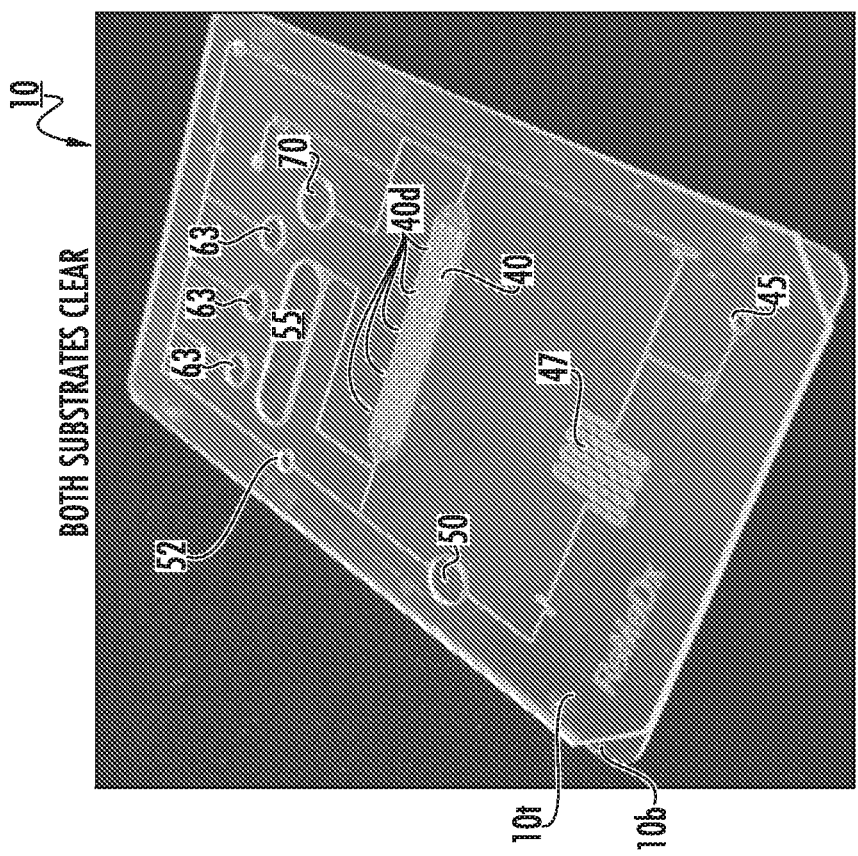
FIG. 4A is a digital photograph of a dual substrate microfluidic chip according to embodiments of the present invention.

Referring to FIGS. 4A and 4B, the microfluidic chip 10 can comprise a plurality of stacked layers, typically first and second substrate layers attached together. FIG. 4A illustrates that both the top and bottom substrates 10t, 10b can be visually transmissive, typically transparent or translucent. FIG. 4B illustrates that the bottom substrate 10b can be opaque (e.g., opaque black) while the top 10t can be visually transmissive.

The top substrate layer 10t can hold at least a portion of the at least one fluid transport channel 20. The transport channel 20 and other fluidic channels may be an internal channel (encased by the top substrate 10t) or may be formed as an open upper surface in the substrate 10t. If the latter, an overlay or cover may attach to an upper surface of the top layer 10t to seal the transport channel 20 or the transport channel 20 may be open to atmosphere over its length or a portion thereof. The bottom substrate layer 10b can hold the bead well array 40. As discussed above, vias and/or fluid intake/exit channels may be used to connect reservoirs or chambers with one or more of external fluid supplies and/or drains.

As shown in FIGS. 4A and 4B, some of the chambers or reservoirs may be open to atmosphere/environmental conditions, including sample intake 45, bead storage 50, secondary reagent incubation chamber 52, waste reservoir 55, secondary reagent inputs 63 and detection substrate and/or PCR master mix 70. An air permeable membrane or membranes 35, 135 can reside over these features/components.

The top and/or bottom substrates 10t, 10b can comprise any suitable material and can be rigid, semi-flexible or flexible. The substrate of the bottom and top layers 10t, 10b can be the same or different materials. The top layer and/or the bottom layer 10t, 10b can comprise silicon, glass, hard plastic, hard polymeric material, a flexible polymeric material, or any hybrid or composite of such materials. Freezing can be used to modulate fluid flow on microfluidic chips through freeze-thaw valves 22. The microfluidic chips 10 can hold one or more primary transport and secondary fluidic buffer and/or reagent channels in a substrate that is elastic/flexible (e.g. polydimethylsiloxane) and/or in a substrate that is inelastic/inflexible (e.g. glass and hard plastic).

FIG. 5 illustrates a microfluidic chip 10 with an air permeable membrane 35, 135. The membrane 35 can, in some embodiments reside over the waste reservoir 55, secondary reagent inputs 63, and detection substrate and/or PCR master mix 70. The membranes 35, 135 can comprise PTFE or other suitable materials and may be "air-only" membranes. The term "air-only" means allowing gas to escape or transverse the membrane while allowing no liquid or particulate matter to pass through under applied pressure differentials of zero to at least 1 psi (or greater, such as to 2, 3, 4 or 5 psi).

FIG. 5B illustrates beads dried down in the bead storage/sample incubation chamber 50 without the air-permeable membrane 135 in position over the chamber 50.

In some particular embodiments, the top substrate 10t can be injection molded with the fluidic channel 20 and other fluid channels. The transport channel 20 can, for example, comprise a 250 µm wide, 250 µm deep channel. The sample metering channel 47 can be wider, typically by between 20-60%, such as about 50% wider than the flow channel 20 on either end of the sample metering channel 47. In some embodiments, the metering channel 47 can be about 500 µm wide and translate up and down a plurality of times before merging back into a straight segment of the channel 20. The array chamber 40 can be relatively shallow, e.g., more shallow by 10-50% than the transport channel 20 between the metering channel 47 and the array 40, such as about 200 µm deep. The array 40 can include physical structures such as laterally and longitudinally spaced apart dividers 40d in the array chamber 40c to keep the chamber from collapsing during bonding of the top substrate 10t to the bottom substrate 10b. The dividers 40d can facilitate control of fluid flow through the wide array chamber 40.

The bottom substrate 10b can be either visually transmissive, e.g., transparent or clear, or opaque, typically opaque black and is also typically plastic. The bottom substrate 10b can contain an array 40 of between about 1-2 million "slit" or "comet" shaped bead and reaction wells. The array 40 can hold about 2 million cylindrical wells. Holes in the top substrate 10t can be used as reservoirs. They can contain dried beads and/or dried reagents.

Once covered with one or more air permeable (filter) membranes 35, 135, the holes (e.g., access apertures or vias) allow air to be vented when a reader forces buffer into the chip 10. Vacuum on a waste reservoir 55 can be used with the freeze-thaw valves 22 to draw rehydrated reagents into the incubation chamber(s) and/or reaction chamber(s) 50, 52. Oil or other suitable sealing agent via input 66 (FIGS. 2A-2C, 3A-3C) can be used to seal individual reactions from one another before imaging the bead array 40 to readout a fluorescence signal. Beads can be loaded and moved through the chip 10 using actuator arms with magnets attached to them as is well known to those of skill in the art.

A buffer 60f (FIGS. 2A, 3A) comprising INAs (e.g., an INP and/or functional fragment thereof and/or a microorganism comprising the same) can be flowably introduced into the transport channel 20 from buffer input 60 (FIG. 2A, 3A), typically after the microfluidic chip 10 is placed in thermal contact with the at least one cooler 25. More typically, the microfluidic chip 10 is placed in position in a test fixture/mounting assembly to be in thermal contact with a plurality of spaced apart thermoelectric coolers 25t, positioned at defined positions, then the buffer with solvated INAs 60f is flowably introduced into the microfluidic chip 10 to reside/fill the fluidic channels, including channel 20 and reagent inputs 63i.

The freeze-thaw valves 25 can be operated by setting a cooler 25, such as the TECs 25t, to defined temperatures for a "freeze" operation/mode, typically between −100 degrees C. and −1 degrees C. In some embodiments, the freeze temperature can be between about −45° C. (estimated steady state internal temperature of −32° C.) and about −20° C. (estimated steady state internal temperature of −11° C.). Temperatures below −45 degrees C. may also be used, in some embodiments the temperatures can be about −50 degrees C. or above to −1 degree C. Temperatures above −20 degrees C. may be used. Different freeze actuations of one or more FTVs 22 can have different temperature and/or time settings. At −45° C., INA-containing buffers are found to freeze more than twice as quickly than an INA-free control, as well as more reproducibly. At −20° C. applied to external surface of the chip, the INA-containing buffers exhibited concentration-dependent effects in terms of freeze time, while INA-free buffers did not freeze at all in the observed timeframe. It is contemplated that embodiments of the invention may be used to facilitate microfluidic freeze-thaw valving that can reduce the freeze time and temperature requirements of the system over conventional FTV systems. The freeze-thaw systems can be compatible with different microfluidic substrates including inflexible/inelastic materials such as glass and silicon and may expand the number of device designs available to users.

While certain embodiments described herein propose INAs solvated in a primary (working) buffer such as via buffer input 60 (FIGS. 2A, 3A, for example), other ways of providing and/or introducing INAs to a fluidic microchip 10 are also contemplated. For example, one or more fluidic channels of a microfluidic chip 10 may be filled (partially or totally) with INA-containing buffer and then dried, thus passively coating channels or channel segments with the INAs. These proteins may then be used to nucleate freezing after rehydrating the device. While an indefinite number of valving steps may not be possible with this method if the proteins are washed away over time, it may work well if a few actuations are used for the device's operation. Examples of this include devices in which freezing is only required during early phases of the device's use, or there are otherwise only a few freezing steps with minimal exchange of buffer that would wash away the INAs.

It may also be possible to covalently attach INAs to channel walls, e.g. with PEG-Sulfo-NHS linking chemistry, and achieve a similar effect with the advantage of fixed nucleating locations with resistance to removal by washing alone.

Targeted deployment of the INAs may also be possible through noncovalent attachments. One instance of this would be coupling streptavidin to the INAs (e.g., either directly during their recombinant expression, or covalently afterwards) and biotin to the regions of the device in which the INAs are desired. The streptavidin-modified INAs would then strongly couple to the areas in which they are desired. Another instance of non-covalent targeted deployment might involve modifying regions of the device with a target molecule, then coupling INAs to antibodies or aptamers that bind to sites on the target molecule. Large particles such as polystyrene microspheres might also be used as carriers for INAs, following their attachment (either covalent or passive) to the particles. Additionally, the INAs may be adsorbed to a microfluidic channel wall by hydrophobic or hydrophilic surface interactions or other non-covalent or electrostatic forces. Finally, if a system does not require the protein to be extracted and solvated, the extraction process may be forgone entirely in place of using whole organisms (e.g., intact *P. syringae*) or their INA-containing membranes. Use of the intact organisms or membranes may be necessary for systems in which the warmest possible ice nucleation temperatures (approximately −2° C. to −6° C.) are needed, as >99.9% of these nucleation sites may be lost after removing the INPs from cell membranes.

Freezing of solutions (e.g., aqueous solutions) using freeze-thaw valves with INAs can be initiated at higher temperatures relative to known conventional microfluidic chips without such INAs. The INAs may optionally be harvested from bacteria as a fluid additive. The freezing process can occur at relatively warm temperatures compared to those required in the absence of the INAs. INAs can initiate the ice crystallization process at temperatures of about −2° C., whereas water can be supercooled to approximately −40° C. and not crystallize in the absence of nucleation sites (e.g., in pure water or in microfluidic devices with smooth channels). In addition and/or alternatively to triggering freezing at warmer temperatures, INAs can significantly reduce the average time water must be held below the freezing point before crystallization occurs. Implementation of the INA freeze-thaw processing technique can be used to allow precise fluid control with simple and easy to manufacture chip architectures without requiring moving valve parts, greatly reducing fabrication and operation costs.

In some embodiments, an INA may be used in a method of preparing a sample. For example, an INA may be used to improve freezing of a sample in a sample metering loop in a fluidic analysis device as part of sample preparation including, but not limited to, cell lysis. In some embodiments, a sample may comprise a plurality of cells, and at least a portion of the plurality of cells may be lysed by electronically selectively cooling the sample metering loop using at least one freeze thaw valve to freeze the at least one freeze thaw valve and/or at least a portion of the sample in the sample metering loop. In some embodiments, the sample metering loop and/or at least one freeze thaw valve may be heated to thaw the sample metering loop, the at least one freeze thaw valve, and/or at least a portion of the sample. Heating the sample metering loop and/or at least one freeze thaw valve may be active heating or passive heating. Active heating can be electronically selectively heating the sample metering loop and/or at least one freeze thaw valve. Active heating can use a heat source (e.g., a thermo-electric source) to increase the temperature of the freeze thaw valve and/or sample metering loop. Passive heating is when a freeze thaw valve and/or sample metering loop is allowed to warm up (e.g., thaw) to room temperature based on the surrounding environment without the active application of heat from a heat source.

Figure 6:
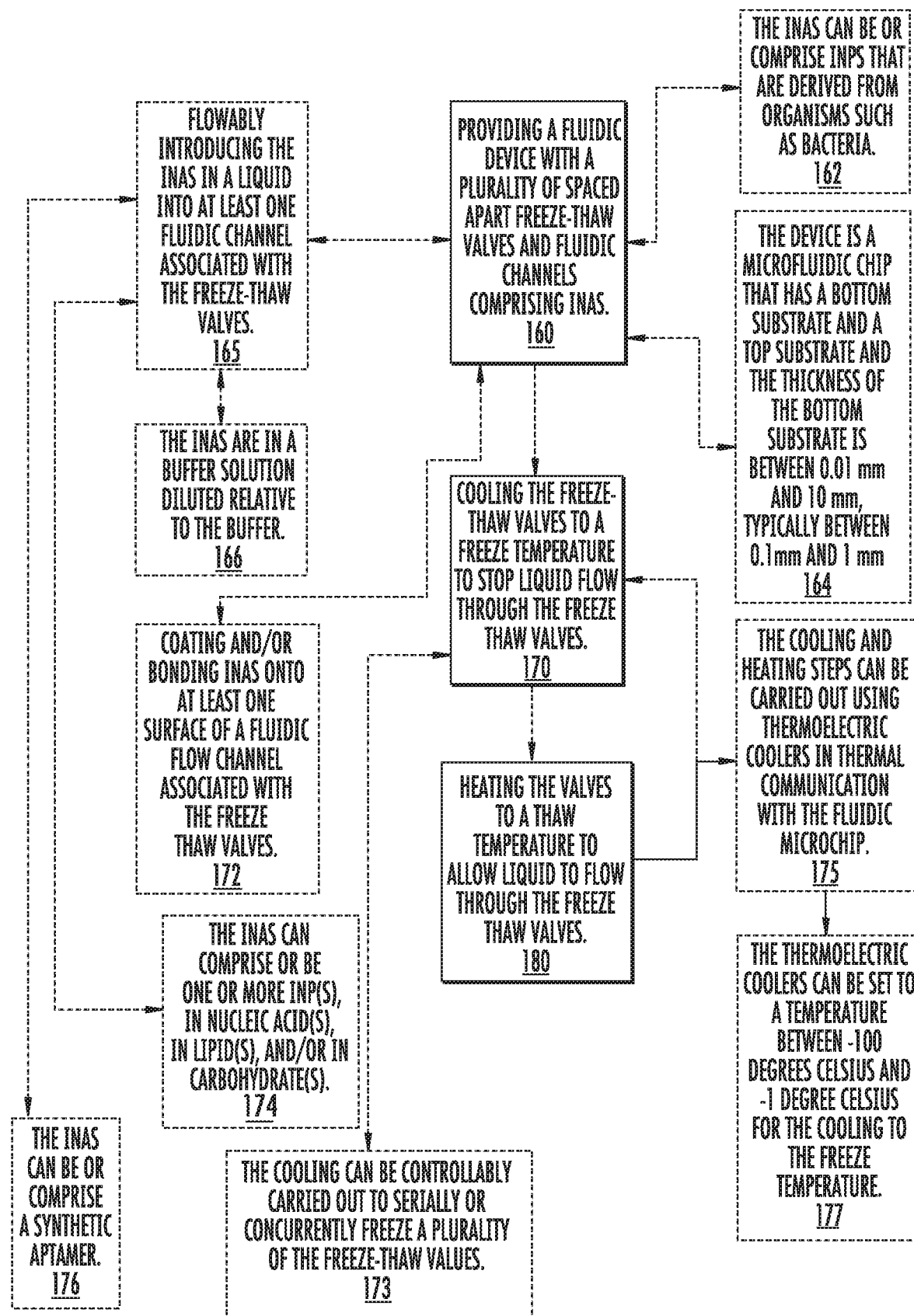
FIG. 6 is a flow chart of exemplary actions of methods for processing and/or analyzing analytes that can be carried out according to embodiments of the present invention.

FIG. 6 illustrates exemplary actions that can be carried out for methods of processing and/or analyzing analytes. As shown, a fluidic device with a plurality of spaced apart freeze-thaw valves and fluidic channels comprising INAs is provided (block 160). The freeze thaw valves are cooled to a freeze temperature to stop liquid flow through the freeze thaw valves (block 170). The freeze thaw valves are heated to a thaw temperature to allow liquid to flow through the freeze thaw valves (block 180). Heating of a freeze thaw valve may be active or may be passive.

The INAs can be harvested and/or derived from organisms such as bacteria (block 162).

The INAs can be flowably introduced in a liquid into at least one fluidic channel associated with the freeze-thaw valves (block 165). The flowable introduction can be in a single or successive defined amount or bolus (i.e., batch), or carried out in a continuous manner. The amounts of the INAs may be constant, increase or decrease over successive processing operations in a single microfluidic device.

The device can be a microfluidic chip that has a bottom substrate and a top substrate (attached directly or indirectly together). The bottom substrate can have a thickness between 0.01 mm and 10 mm (block 164).

The cooling and heating can be carried out using thermoelectric coolers (TECs) in thermal communication with the fluidic microchip (block 175). Some of the TECs can reside adjacent the bottom substrate and some may reside adjacent to the top substrate. The TECs can be set to a temperature of between −100 degrees C. and −1 degree C. for the cooling to the freeze temperature (block 177).

The extracted INAs solution can be added to a buffer solution diluted in any suitable amount, by way of example only, e.g., 1:10 to 1:10,000, relative to the buffer (block 166). In some embodiments, an INA may be present in a buffer solution in an amount of about 1 molecule or organism per µL to 10 billion molecules or organisms per µL and/or any range and/or individual value therein. In some embodiments, an INA may be present in a buffer solution in an amount of about 1 nanomolar to 100 millimolar, including 10-50 nM, in some particular embodiments.

The INAs can be provided as a coating and/or bonded to at least one surface associated with a fluidic flow channel associated with the freeze thaw valves (block 172). The bonded/coated surface(s) can be on-device or in a conduit or other device associated with a travel path in fluid communication with the fluidic device.

The cooling can be controllably carried out to serially or concurrently (i.e., selectively) freeze some or all of the freeze-thaw valves (block 173). Similarly, the heating can be controllably carried out to serially or concurrently (i.e., selectively) heat some or all of the freeze-thaw valves. Some or all of the freeze-thaw valves may be actively heated or passively heated.

The INAs can comprise or be one or more INP(s), ice-nucleating (IN) nucleic acid(s), IN lipid(s), and/or IN carbohydrate(s) (block 174).

The INAs can comprise or be one or more synthetic aptamer(s) (block 176).

FIG. 7 illustrates an exemplary automated test system 200 with an integrated reader 300 and holding assembly 250 for a microfluidic chip 10. The system 200 can be have a support module 200*h* with control inputs for coolers 25, such as voltage and fluid inputs, for example. Wiring and tubing W, T can connect the holding assembly 250 to the control/fluid inputs of module 200*h*. The voltage and/or fluid inputs can be integrated into the same module that holds the microfluidic chip 10 or may be a separate cooperating sub-assembly or module 200*h*, for example. The system 200 can include a base 202 that supports the mounting assembly 250 and reader 300. The base 202 can also support secondary reagent fluids 63*f* and/or a buffer, typically comprising INAs for fluidic introduction to a fluidic flow channel for operation with a freeze thaw valves 22.

The system 200 can include or be in communication with a controller 200*c* (FIG. 8) with a display 210 and a graphic user interface (GUI) 260 (FIG. 9) for allowing a user to select timing/temperature inputs for controlling and/or scripting the freeze thaw valves 22 operation. Default operations and/or electronically selectable defined menus of operations for sets of freeze thaw valves for particular samples or types or chip size and/or configurations can be preset for ease of use. The display 210 may be onboard the system 200, module 200h, or be remote from the system 200 and/or module 200h.

Figure 8:
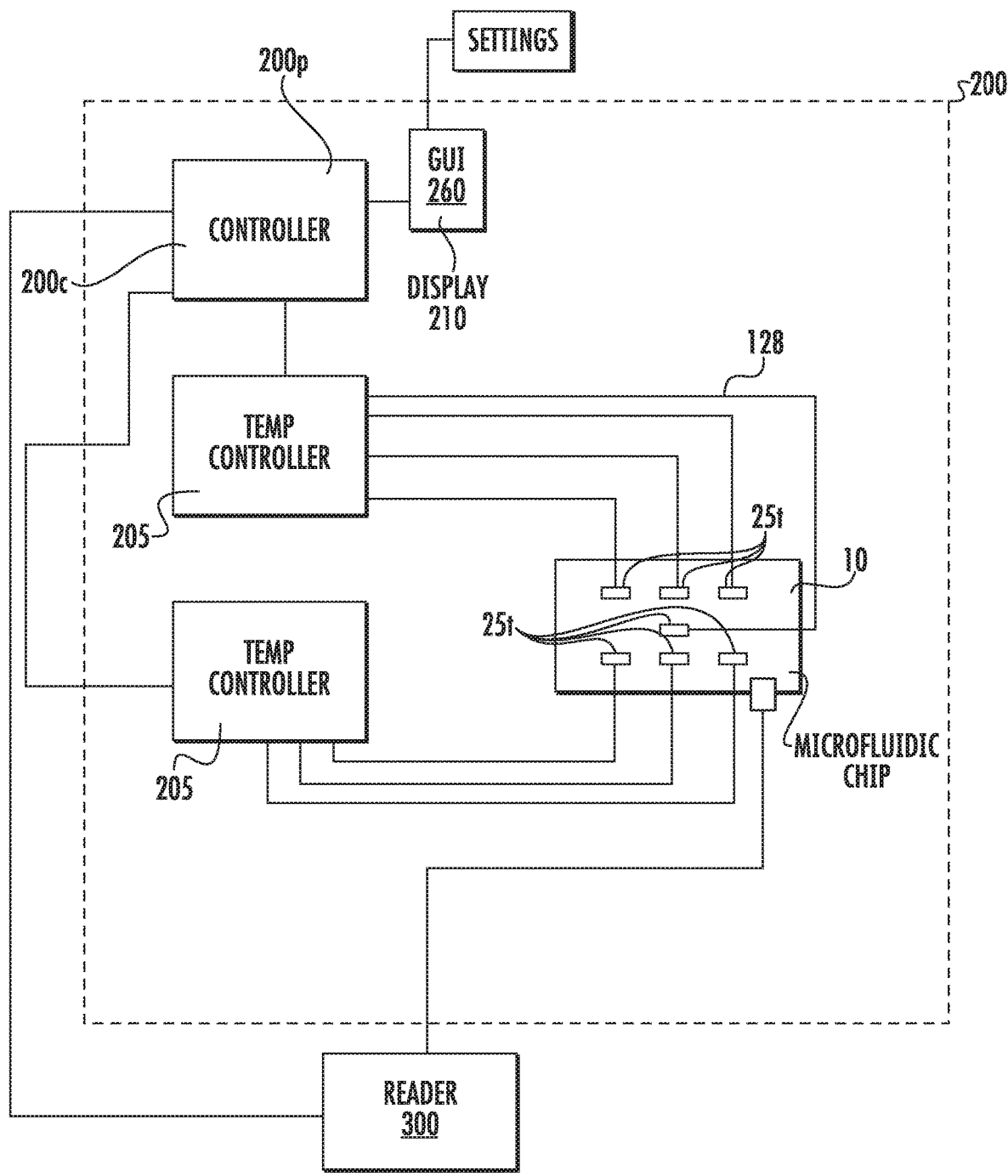
FIG. 8 is a schematic illustration of an exemplary system with freeze-thaw valves for fluidic control according to embodiments of the present invention.

Referring to FIG. 8, the system controller 200c can be onboard the system 200 or remote from the system and be configured to provide the GUI 260 for allowing a user to adjust settings such as a temperature parameter or script for one or more and/or sets of different FTVs 22. The system controller 200c may be held totally in a local computer, partially in a local computer and/or distributed over a plurality of databases/servers (e.g., be CLOUD based). The term "computer" is used broadly to include any electronic device, typically comprising at least one digital signal processor, allowing for control and communication with the FTVs 22 to control operation. The computer can be local or remote from a site with the module 200h.

The display 210 can be onboard or remote from the system 200. The display 210 can comprise a display associated with a pervasive computing device such as a smartphone, electronic notebook and the like. The GUI 260 may be provided by an APP (the APP typically has defined functionality accessible via one or more icons). The system controller 200c can control one or more temperature controllers 205 for one or more of the coolers 25, e.g., the TEC elements 25t. The temperature controller 205 can be any suitable temperature controller such as a Wavelength Electronics (Bozeman, Mont.) PTC5K-CH 5 A temperature controller, which can be controlled by a National Instruments data acquisition/voltage output card that, in turn, can be controlled by a computer running a LabVIEW or other suitable operating program. Each TEC element 25t can have its own PTC5K-CH controller or sets or all can share a temperature controller. In some embodiments, a custom temperature control circuit can be used to control the operation of the TEC elements 25t. Electrical paths 128 can connect the temperature controller(s) 205 to one or more TEC element(s) 25t.

Figure 9:
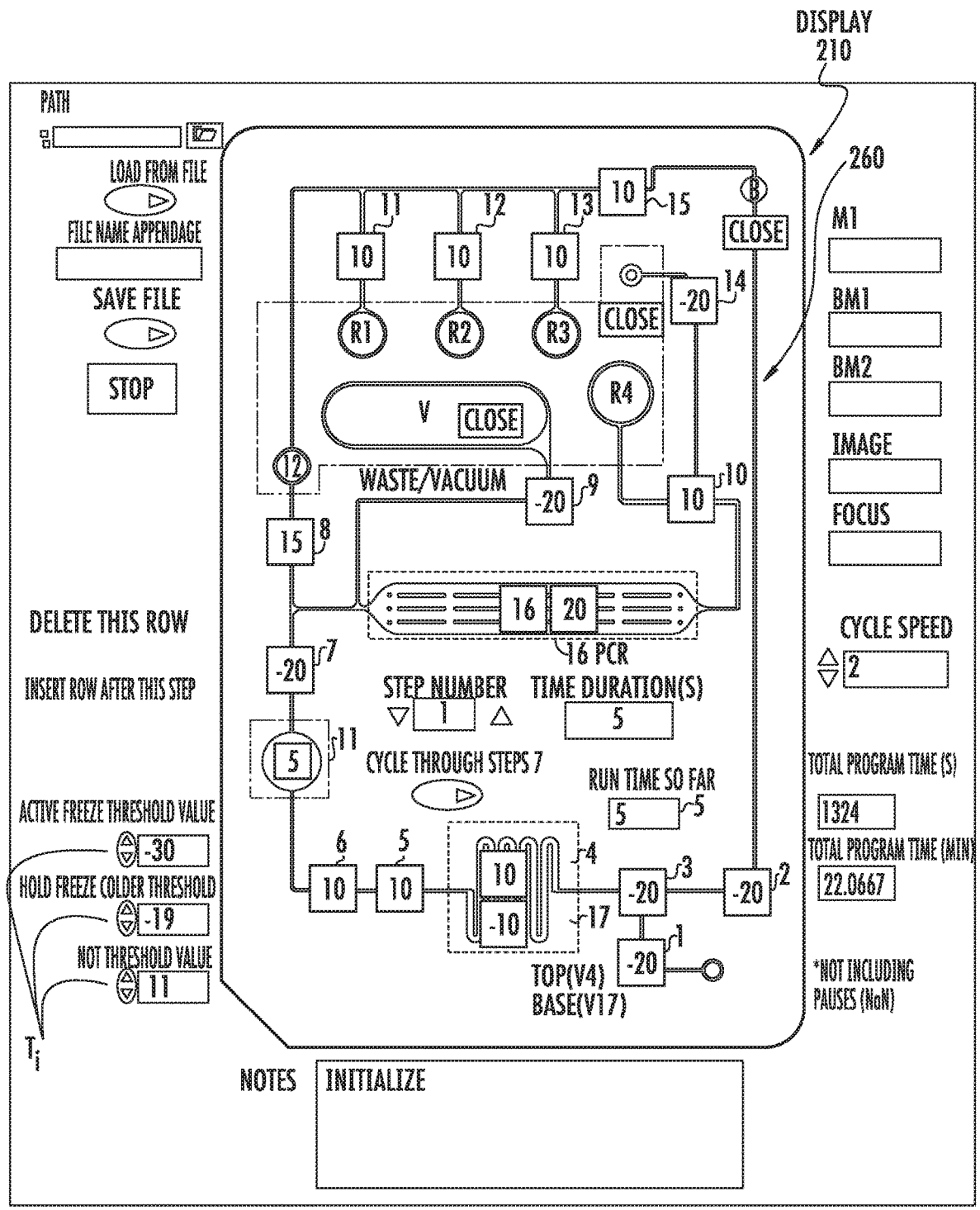
FIG. 9 is an exemplary graphic user interface for controlling freeze thaw valve ON/OFF and/or temperature operation according to embodiments of the present invention.

FIG. 9 illustrates the intuitive operating screen of a GUI 260 with steps and timing adjustments as well as user-selectable temperature adjustments (Ti) for the freeze thaw valves 22 (valves 10-15, as shown). A graphic representation of the layout of the chip 10 can be presented on the display 210. A user can adjust settings and durations of respective coolers 25 associated with freeze-thaw valves 22 using the GUI 260.

Figure 10:
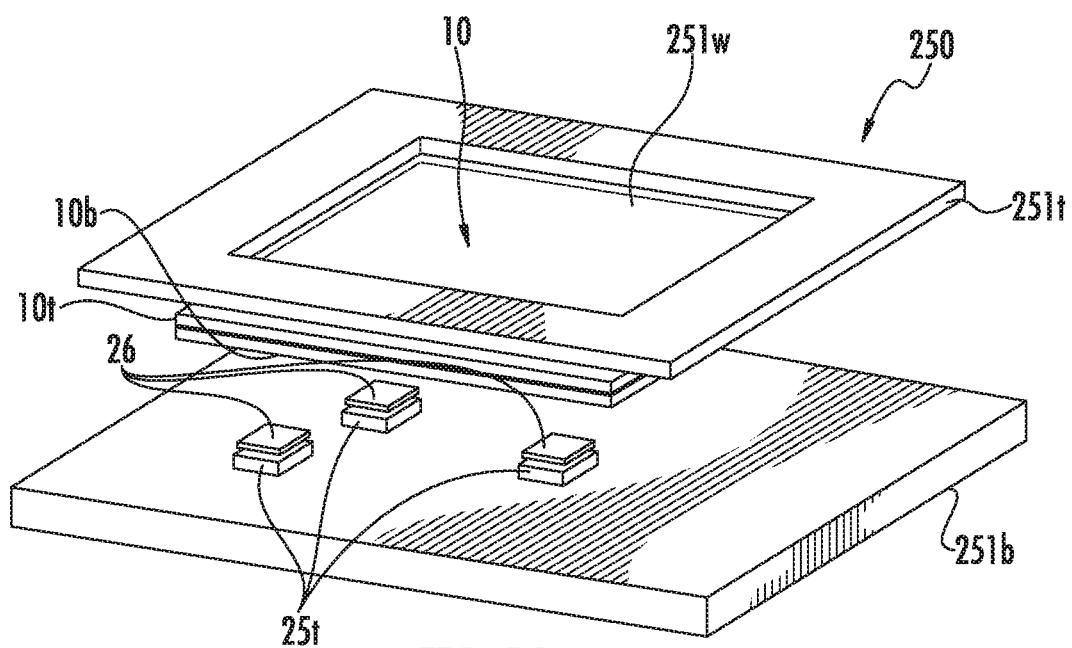
FIG. 10 is an exploded view of an exemplary mounting assembly with TEC mounts for holding a microfluidic chip according to embodiments of the present invention.

FIG. 10 illustrates a mounting assembly 250 for holding the microfluidic chip 10 so that TEC members/elements 25t have appropriate thermal contact with a thermally conductive block or direct contact with a TEC member 25t. The mounting assembly 250 can include a plurality of thermally conductive members 26, such as metal (e.g., copper or other suitable thermally conductive material) shims, that respectively abut the top or bottom substrate 10t, 10b of the chip 10 on one side and a TEC 25t on the other. In some embodiments, a thermally conductive material and/or block 26 can be attached to the substrate 10t and/or 10b, then placed into the mounting assembly 250 in thermal communication with the TEC members 25t. As shown in FIG. 10, the TEC members 25t can be placed on a holding substrate (e.g., plate) 251b aligned with valve locations on the microfluidic chip 10.

Foil or thermally conductive coatings can be applied to the substrate 10b, 10t, at least in regions of the freeze thaw valves 22 (not shown).

The TEC members 25t and mounting devices can be configured to allow for easy replacement and the modular design can facilitate future changes in designs.

As shown in FIG. 10, the mounting assembly 250 can include a rigid top plate 251t that can have a perimeter that extends about a window 251w. FIG. 8 also illustrates that the system 200 can include a computer 200c with a circuit and/or at least one processor 200p that can obtain the analysis data for the analyte in the transport channel 20. The term "computer" is used broadly to include any electronic device, typically comprising at least one digital signal processor, to control operation. The computer can be local or remote from a site with the device 10.

The reader 300 can include a detector and excitation source that can take a series of images of an analyte molecule in the transport channel 20 and/or array 40. The reader 300 for the system 200 can include an excitation light source (typically for generating light that excites fluorescently labeled molecules) (which can optionally include a mirror and lens or other objective) and image generating device or detector such as one or more of a camera, photomultiplier tube or photodiode. The objective/lens, where used, can reside under or over a primary surface of the device 10. The electric inputs/outputs and flow operation can reside on an opposing side of the device 10. The device 10 may also be flipped to operate on its side (with the flat primary surfaces being upright or angled) rather than substantially horizontal as shown.

The present invention is explained in greater detail in the following non-limiting Examples.

Use of Ice-Nucleating Proteins to Reduce Valve Actuation Time and Variability at Low Temperatures A blocking buffer suitable for immunoassays (50 mM Tris+10% newborn calf serum+0.1% Tween-20+0.05% sodium azide, pH=7.4) was used to supply a 2 mm thick plastic microfluidic chip containing channels with a 250 µm width and 250 µm depth comprised of two substrates, each with a thickness of approximately 1 mm. The chip was placed atop TECs so that its channels were positioned over the TEC elements (FIGS. 1A/1B) in places where valving was desired. Freezing and thawing of the channel contents were effected on-chip by setting the TECs to −45° C. and +25° C., respectively. It should be noted that the actual temperature seen at the FTV region of the channel was significantly higher than −45° C., as heat loss through the plastic can be modeled to show a resulting steady state temperature of approximately −32° C. Each freeze and thaw event was timed according to bright field microscopic monitoring of the channels, with the time starting upon initiation of the cooling of the TEC from 25° C. or warming of the chip from −45° C. (i.e. the time includes the time required for the TEC to cool or heat itself and the chip). The rapid appearance of ice was used as the endpoint of each freeze event, while its disappearance was used as the endpoint of each thaw event. Decade dilutions (1:10, 1:100, 1:1,000, 1:10,000) of the INP extract were then prepared in the Tris buffer, and the same timing experiment was carried out with each of these samples. INP-free Tris buffer required an average time of 37 s with a standard deviation of 2.0 s (estimated channel temperature=−32° C.). Addition of the INP extracts significantly impacted the freeze time and reproducibility, and no concentration-dependent effects were observed across the four INP concentrations tested, as freezing occurred in approximately 18-20 s in all cases with a standard deviation of approximately 1 s.

Using temperature measurements from an IR camera with a single 1 mm thick plastic substrate atop the TEC, the internal temperature is estimated to be at ≈−22° C. at the time of freezing. Ten freeze/thaw trials were run for each sample, and these data are shown in FIG. 11.

Figure 12:
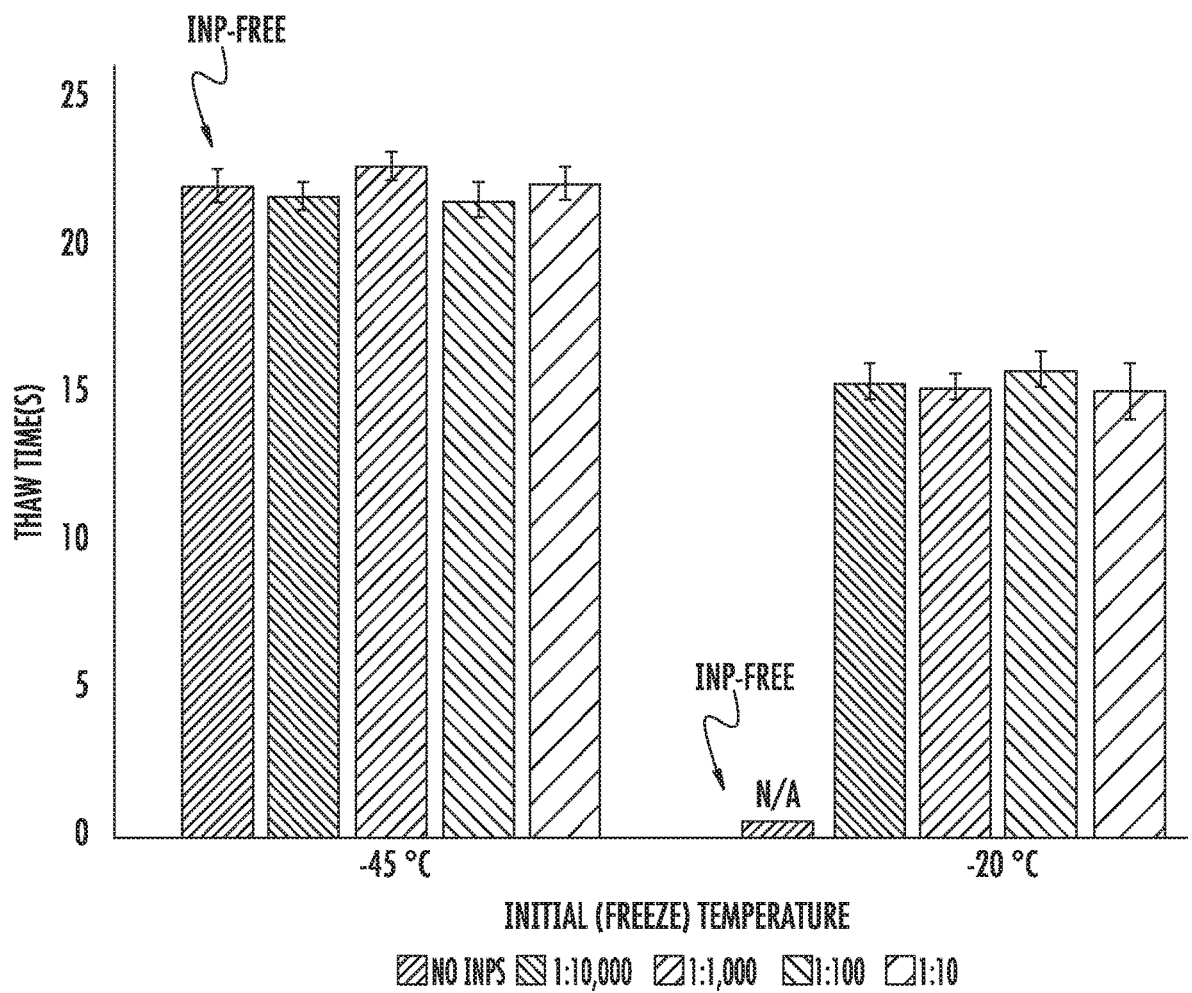
FIG. 12 is a graph of thaw time (seconds) versus temperature used to freeze the sample for five different INP extract dilutions in Tris buffer according to embodiments of the present invention. The left most bar for each set of bars is for a buffer with no INP (INP-free). Thaw times are not applicable at the −20 degree C. freeze temperature for the INP-free buffer because it did not freeze at that temperature. The error bars illustrate one standard deviation in each direction.

Thaw times were completely unaffected by INP concentrations, being approximately 20-22 s in all cases, including for the INP-free buffer (as shown in FIG. 12).

Figure 11:
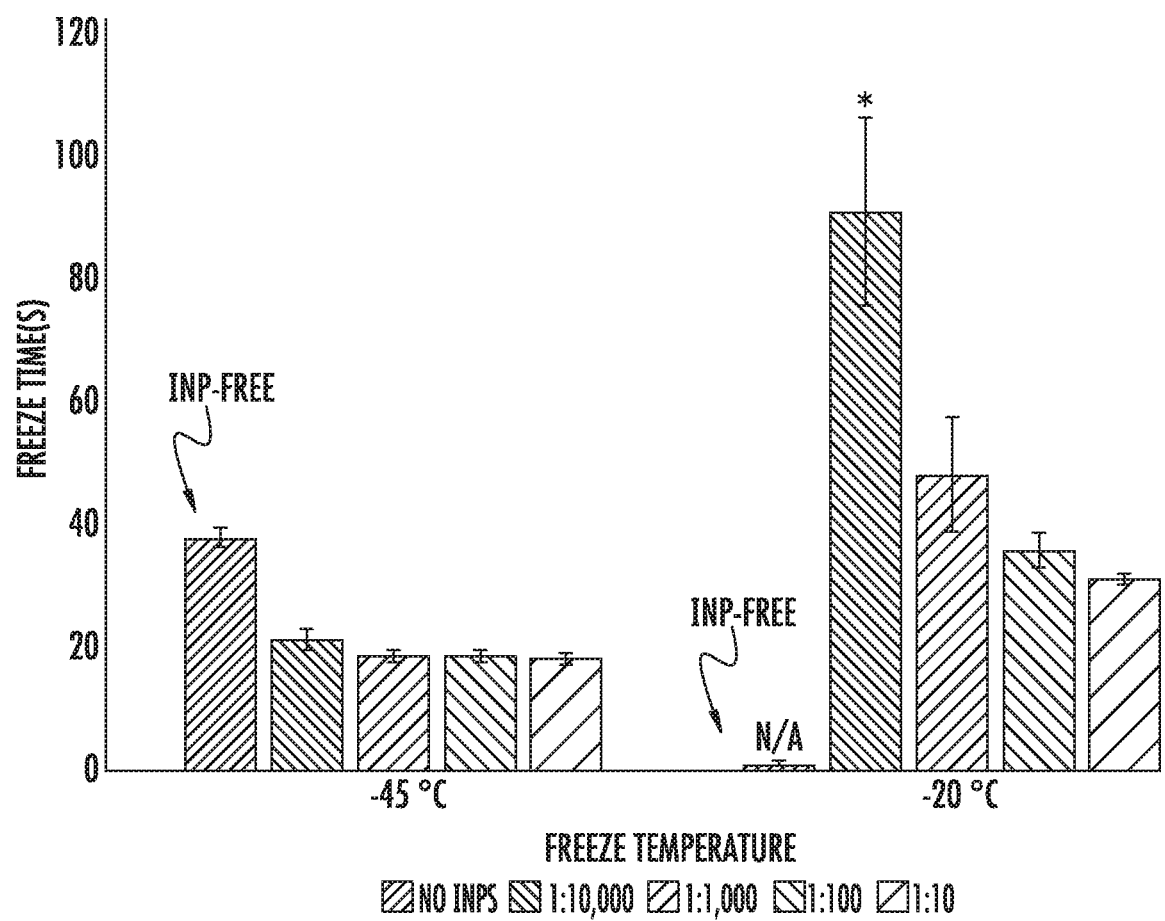
FIG. 11 is a graph of freeze time (seconds) versus temperature for a buffer with no INP ("INP-free") shown as the left most bar at each temperature) and for different INP extract dilutions in Tris buffer according to embodiments of the present invention. The INP-free buffer did not freeze at −20 degrees C. in the time allotted. The error bars illustrate one standard deviation in each direction.

FIG. 11 illustrates the effect of INP extract dilution on freeze times in Tris blocking buffer. Compared to an INP-free control, all four INP extract dilutions froze approximately twice as quickly at −45° C. with no concentration-dependent effects. At −20° C., INP-free buffer did not freeze during five 30 min trials. Required freeze time and standard deviation (both absolute and percent relative) decrease as a function of INP concentration at this temperature. The 1:10,000 INP buffer at −20° C. (*) froze only ten times in fifteen 3 min trials. N=10 for −45° C. trials and N=15 for −20° C. trials. Error bars represent one standard deviation in each direction.

FIG. 12 illustrates thaw times for five different INP concentrations in Tris buffer. Initial temperature refers to the temperature used to freeze the channel, as channels were set to thaw directly from this temperature. No concentration-dependent effects are evident for thawing at either temperature. Thaw times were not applicable for the INP-free buffer at −20° C. because it did not freeze at that temperature. N=10 for −45° C. trials and N=15 for −20° C. trials. Error bars represent one standard deviation in each direction.

Use of Ice-Nucleating Proteins to Reduce Temperature Requirements for Warmer Valving Temperatures The system and INP extract dilutions used for low-temperature free-thaw valving were tested again in the same manner described for the low-temperature tests, except the freezing temperature used was −20° C. (estimated steady state temperature of −11° C. inside the channel). Fifteen trials were run, and the data are shown in FIG. 11. The INP-free blocking buffer was not observed to freeze during five 30 min trials with the TECs set at −20° C. All INP-containing samples froze at this temperature with concentration-dependent effects. The 1:10 and 1:100 INP extract dilutions took longer to freeze than at −45° C., with average freeze times of 33 s±2.0 s and 36 s±2.0 s, respectively (estimated channel temperatures of −11° C. in both cases). The 1:1,000 INP extract dilution exhibited behavior similarly to that of Tris buffer at −45° C., with similar freeze times (44 s average) and a large standard deviation (6.5 s). Over fifteen 3 min trials, the 1:10,000 INP extract dilution froze ten times with an average of 91 s with an extremely large standard deviation of 45 s; its shortest freeze time was 41 s and the longest was 174 s. As with the trials at −45° C., the thaw times were not affected by the INP concentration. All trials −20° C. thawed in approximately 15 s with less than 1 s standard deviation. These data are shown in FIG. 12.

Use of Ice-Nucleating Proteins to Reduce Actuation Time in Thin Chips

A final set of experiments was conducted utilizing a thinner chip that was identical to the ones used in the above trials (standard chips) except its bottom substrate thickness was 0.5 mm instead of 1 mm. Freeze times were again tested at −45° C. and −20° C. TEC temperature using Tris buffer with and without INPs. Only the 1:100 dilution of INP extract was tested in these experiments. The effect of halving the substrate thickness was pronounced. At −45° C., freeze times were 13 s±0.48 s and 22 s±0.92 s with and without INPs, respectively, versus 19 s+1.1 s and 37 s±2.0 s for the standard chips under those conditions. At −20° C. with INPs, freezing required 18 s±0.74 s, which is approximately the same as −45° C. with INPs in a standard chip. As with standard chips, no freezing was observed at −20° C. in the allotted time without INPs. These data and a comparison to relevant standard chip data are shown in FIG. 13.

Figure 13:
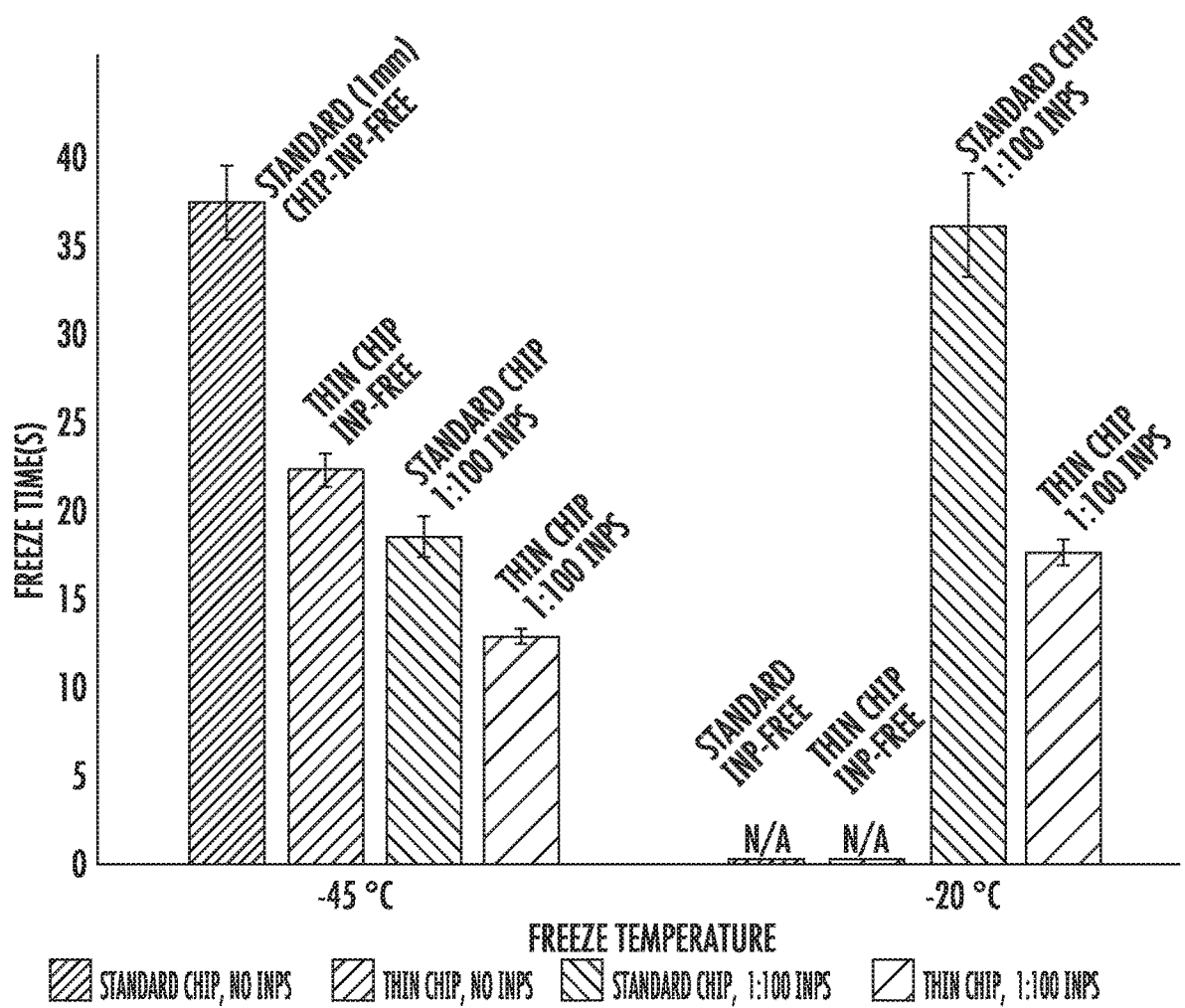
FIG. 13 is a graph of freeze time (seconds) versus temperature used to freeze a sample for different chip thicknesses and different INP extract dilutions according to embodiments of the present invention. Thaw times are not applicable at the −20 degree C. freeze temperature for the INP-free buffer for the standard and thin thickness microfluidic chips because the sample did not freeze at that temperature. The error bars illustrate one standard deviation in each direction.

FIG. 13 illustrates a comparison of freeze times between standard (1 mm substrate) and thinner chips (0.5 mm substrate) with and without INPs. For each freeze temperature and buffer condition, freezing occurred substantially faster in a thin chip than a standard chip, except at −20° C. with no INPs, where neither chip content froze in the allotted time. The fastest observed freeze times occurred in the thinner chip with INPs at −45° C. (~13 s vs. ~19 s for standard chips). The largest performance difference occurred at −20° C., where the thin chip froze approximately twice as fast as the standard chip (~18 s vs. ~36 s). The temperature increase from −45° C. to −20° C. added only ~5 s to the required freeze times for the thin chip with INPs, whereas it added ~18 s to the required freeze time for standard chips, effectively doubling it. N=10 for all thin chip trials. The error bars represent one standard deviation in each direction.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A fluidic analysis device, comprising:
   at least one fluid channel comprising at least one freeze thaw valve and at least one ice nucleating agent (INA), wherein the at least one INA is a carbon-containing INA, and wherein the at least one INA nucleates ice formation,
   wherein the at least one INA comprisese an ice-like lattice structure.

2. The fluidic analysis device of claim 1, wherein the at least one INA is extracted or derived from an organism.

3. The fluidic analysis device of claim 1, further comprising first and second substrates attached together to define a microfluidic chip as the fluid analysis device with the at least one fluid transport channel and a plurality of spaced apart freeze thaw valves along the at least one fluid transport channel as the at least one freeze thaw valve.

4. The fluidic analysis device of claim 1, in fluid communication with a liquid buffer comprising the at least one INA, wherein the at least one INA is flowably introduced into a fluid port on the fluidic analysis device, and wherein the at least one INA is present in the liquid buffer in an amount from 1 molecule/µL to 10 billion molecules/µL, or in a concentration of about 1 nM to about 1 mM.

5. The fluidic analysis device of claim 1, wherein the at least one freeze thaw valve is a plurality of spaced apart freeze thaw valves, each comprising a thermoelectric cooler in thermal communication with a defined region of the at least one fluid channel, and wherein the at least one fluid channel has at least a segment that is sized to be a microfluidic or nanofluidic channel.

6. The fluidic analysis device of claim 1, wherein the at least one fluid channel comprises a primary transport channel and at least one reagent channel, and wherein the fluidic analysis device comprises a sample input, a buffer input and a bead well array, all in fluid communication with the primary transport channel, with the at least one freeze thaw valve comprising a plurality of spaced apart freeze thaw valves in fluid communication with the primary transport channel and/or at least one reagent channel.

7. The fluid analysis device of claim 6, further comprising a bead storage/sample incubation chamber, a waste reservoir and at least first and second freeze thaw valves that are spaced apart.

8. The fluid analysis device of claim 1, wherein the at least one INA comprises a structure that aligns water molecules into an ice-like lattice.

9. A fluidic analysis device, comprising:
at least one fluid channel comprising at least one freeze thaw valve and at least one ice nucleating agent (INA), wherein the at least one INA is a carbon-containing INA, and wherein the at least one INA comprises an ice-nucleating protein and/or a functional fragment thereof, an ice-nucleating nucleic acid, an ice-nucleating lipid, and/or an ice- nucleating carbohydrate.

10. The fluidic analysis device of claim 2, wherein the at least one INA comprises the ice-nucleating protein (INP) and/or the functional fragment thereof.

11. The fluidic analysis device of claim 10, wherein the INP and/or the functional fragment thereof is encoded by at least one gene selected from the group consisting of: iceE, iceH, inaA, inaE, inaF, inaK, inaPb, inaQ, inaU, inaV, inaW, inaX, and inaZ, and wherein the gene is found in or obtained from an organism selected from the group consisting of: *Pseudomonas syringae*, Ps. *fluorescens* KUIN-1, *Erwinia herbicola*, *E. uredovora*, *Pantoea ananatis*, *Xanthomonas campestris*, *E. carotovora*, Ps. *antarctica*, Ps. *aeruginosa*, Ps. *putida*, Ps. *viridiflava*, Pa. *agglomerans*, *E. ananas*, and Ps. *borealis*.

12. The fluidic analysis device of claim 9, wherein the at least one fluid channel comprises at least one fluid channel with the at least one INA bonded and/or coated to a surface thereof.

13. A method of analyzing a target analyte, comprising:
providing a fluidic analysis device with at least one fluidic channel in fluid communication with at least one freeze thaw valve;
introducing at least one ice nucleating agent (INA) into the at least one fluidic channel, wherein the at least one INA contains a carbon atom, and wherein the at least one INA nucleates ice formation; and
electronically selectively cooling the at least one freeze thaw valve to freeze the at least one freeze thaw valve using the at least one INA, wherein the at least one INA comprises an ice-like lattice structure.

14. The method of claim 13, wherein the at least one freeze thaw valve is a plurality of spaced apart freeze thaw valves, and wherein the method comprises setting coolers thermally communicating with the at least one fluidic channel to a temperature between −100 degrees C. and −1 degree C. to freeze the freeze thaw valves.

15. The method of claim 13, wherein the fluidic device is a fluidic microchip with a thickness between 0.1 mm and 10 mm, wherein the at least one freeze thaw valve is a plurality of spaced apart freeze thaw valves, and wherein at least some of the freeze thaw valves have thermoelectric coolers set to between about −100 degrees C. and about −1 degree C. for a freeze operation that occurs in three minutes or less, and wherein the electronically selectively cooling is carried out a plurality of times for a respective sample.

16. The method of claim 13, wherein the device is a fluidic microchip, wherein the method further comprises introducing the target analyte into the at least one fluidic channel, and wherein the target analyte is an organic compound or inorganic compound.

17. The method of claim 13, wherein the at least one INA is extracted or derived from an organism.

18. The method of claim 13, wherein the liquid is a buffer, and wherein the at least one INA is present in the buffer.

19. The method of claim 13, wherein the at least one INA is introduced by releasing the at least one INA from a surface comprising a coating of the at least one INA and/or the at least one INA is adsorbed and/or chemically bonded to a surface of the at least one fluidic flow channel.

20. The method of claim 13, wherein the at least one INA is immobilized on or coupled to a solid support.

21. The method of claim 13, wherein the at least one INA comprises a structure that aligns water molecules into an ice-like lattice.

22. A method of analyzing a target analyte, comprising:
providing a fluidic analysis device with at least one fluidic channel in fluid communication with at least one freeze thaw valve;
introducing at least one ice nucleating agent (INA) into the at least one fluidic channel, wherein the at least one INA contains a carbon atom; and
electronically selectively cooling the at least one freeze thaw valve to freeze the at least one freeze thaw valve using the at least one INA,
wherein the at least one INA comprises an ice-nucleating protein and/or a functional fragment thereof, an ice-nucleating nucleic acid, an ice-nucleating lipid, and/or an ice- nucleating carbohydrate.

23. The method of claim 22, wherein the at least one INA comprises the ice-nucleating protein (INP) and/or one or more functional fragments thereof.

24. The method of claim 23, wherein the INP and/or the one or more functional fragment(s) thereof is encoded by at least one gene selected from the group consisting of: iceE, iceH, inaA, inaE, inaF, inaK, inaPb, inaQ, inaU, inaV, inaW, inaX, and inaZ, and wherein the gene is found in or obtained from an organism selected from the group consisting of: *Pseudomonas syringae*, Ps. *fluorescens* KUIN-1, *Erwinia herbicola*, *E. uredovora*, *Pantoea ananatis*, *Xanthomonas campestris*, *E. carotovora*, Ps. *antarctica*, Ps. *aeruginosa*, Ps. *putida*, Ps. *viridiflava*, Pa. *agglomerans*, *E. ananas*, and Ps. *borealis*.

25. A method of preparing a sample, comprising:
providing a fluidic analysis device comprising a sample metering loop and at least one fluidic channel, wherein the sample metering loop and the at least one fluidic channel are in communication with at least one freeze thaw valve;
introducing a sample into the sample metering loop, wherein the sample comprises at least one ice nucleating agent (INA) that contains a carbon atom, wherein the at least one INA nucleates ice formation, and wherein the at least one INA comprises an ice-nucleating protein and/or a functional fragment thereof, an ice-nucleating nucleic acid, an ice-nucleating lipid, and/or an ice-nucleating carbohydrate; and
electronically selectively cooling the sample metering loop using the at least one freeze thaw valve to freeze the at least one freeze thaw valve and/or at least a portion of the sample in the sample metering loop.

26. The method of claim 25, wherein the at least one fluidic channel comprises a primary transport channel and at least one reagent channel, and wherein the fluidic analysis device comprises a sample input, a buffer input and a bead well array, all in fluidic communication with the primary transport channel, and wherein the at least one freeze thaw valve is a plurality of spaced apart freeze thaw valves in communication with the primary transport channel and/or at least one reagent channel.

27. The method of claim 25, wherein the fluidic analysis device further comprises a bead storage/sample incubation chamber and a waste reservoir, wherein the sample metering loop resides between the bead storage/incubation chamber and the sample input.

28. The method of claim 25, wherein the sample metering loop has a volumetric capacity of between about 1μL to about 1 mL and is in fluid communication with first and second freeze thaw valves on respective end portions of the sample metering loop.

29. The method of claim 25, wherein the at least one INA comprises the ice-nucleating protein (INP) and/or one or more functional fragment(s) thereof.

30. The method of claim 29, wherein the INP and/or the one or more functional fragment(s) thereof is encoded by at least one gene selected from the group consisting of: iceE, iceH, inaA, inaE, inaF, inaK, inaPb, inaQ, inaU, inaV, inaW, inaX, and inaZ, and wherein the gene is found in or obtained from an organism selected from the group consisting of: *Pseudomonas syringae*, Ps. *fluorescens* KUIN-1, *Erwinia herbicola*, E. *uredovora*, *Pantoea ananatis*, *Xanthomonas campestris*, E. *carotovora*, Ps. *antarctica*, Ps. *aeruginosa*, Ps. *putida*, Ps. *viridiflava*, Pa. *agglomerans*, E. *ananas*, and/or Ps. *borealis*.

31. A method of preparing a sample, comprising:
providing a fluidic analysis device comprising a sample metering loop and at least one fluidic channel, wherein the sample metering loop and the at least one fluidic channel are in communication with at least one freeze thaw valve;
introducing a sample into the sample metering loop, wherein the sample comprises at least one ice nucleating agent (INA) that contains a carbon atom, wherein the at least one INA nucleates ice formation; and
electronically selectively cooling the sample metering loop using the at least one freeze thaw valve to freeze the at least one freeze thaw valve and/or at least a portion of the sample in the sample metering loop,
wherein the sample comprises a plurality of cells, and wherein electronically selectively cooling the sample metering loop using the at least one freeze thaw valve to freeze the at least one freeze thaw valve and/or at least a portion of the sample in the sample metering loop lyses at least a portion of the plurality of cells.

\* \* \* \* \*

UNITED STATES PATENT AND TRADEMARK OFFICE
CERTIFICATE OF CORRECTION

PATENT NO. : 10,864,520 B2
APPLICATION NO. : 15/742662
DATED : December 15, 2020
INVENTOR(S) : Ramsey et al.

It is certified that error appears in the above-identified patent and that said Letters Patent is hereby corrected as shown below:

In the Specification

Column 8, Line 40: Please correct "250 m/250 µm" to read -- 250 µm/250 µm --

Column 10, Line 16: Please correct "per L" to read -- per µL --

Column 10, Line 19: Please correct "per L" to read -- per µL --

Column 10, Line 20: Please correct "per L" to read -- per µL --

Column 26, Line 60: Please correct "=-32°" to read -- ≈-32° --

In the Claims

Column 28, Line 44, Claim 1: Please correct "comprisese" to read -- comprises --

Column 29, Line 25, Claim 10: Please correct "claim 2" to read -- claim 9 --

Column 32, Line 6, Claim 30: Please correct "and/or Ps. *borealis*" *to* read -- and Ps. *borealis* --

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*